(12) United States Patent
Bonadio et al.

(10) Patent No.: US 8,187,178 B2
(45) Date of Patent: May 29, 2012

(54) INSTRUMENT ACCESS DEVICE

(75) Inventors: Frank Bonadio, Bray (IE); John Butler, Blackrock (IE); Trevor Vaugh, Birr (IE); Shane J. MacNally, Delgany (IE)

(73) Assignee: Atropos Limited, Bray County Wicklow (IE)

( * ) Notice: Subject to any disclaimer, the term of this patent is extended or adjusted under 35 U.S.C. 154(b) by 968 days.

(21) Appl. No.: 12/133,827

(22) Filed: Jun. 5, 2008

(65) Prior Publication Data

US 2009/0036745 A1 Feb. 5, 2009

Related U.S. Application Data

(60) Provisional application No. 60/924,918, filed on Jun. 5, 2007, provisional application No. 60/935,625, filed on Aug. 22, 2007, provisional application No. 60/996,760, filed on Dec. 4, 2007.

(51) Int. Cl.
*A61B 1/32* (2006.01)
(52) U.S. Cl. ...................................................... 600/208
(58) Field of Classification Search .......... 600/201–208, 600/235; 623/17.11–17.16
See application file for complete search history.

(56) References Cited

U.S. PATENT DOCUMENTS

| | | |
|---|---|---|
| 1,157,202 A | 10/1915 | McLeland |
| 1,598,284 A | 8/1926 | Kinney |
| 1,810,466 A | 6/1931 | Deutsch |
| 2,219,564 A | 10/1940 | Reyniers |
| 2,305,289 A | 12/1942 | Coburg |
| 2,695,608 A | 11/1954 | Gibbon |
| 2,835,253 A | 5/1958 | Borgeson |
| 2,853,075 A | 10/1958 | Hoffman |
| 3,039,468 A | 6/1962 | Price |
| 3,111,943 A | 11/1963 | Orndorff |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |

(Continued)

FOREIGN PATENT DOCUMENTS

DE  37 39 532  12/1988

(Continued)

OTHER PUBLICATIONS

International Search Report for PCT/IE2008/00062 dated Oct. 21, 2008.

(Continued)

*Primary Examiner* — Eduardo C Robert
*Assistant Examiner* — James Palmer
(74) *Attorney, Agent, or Firm* — Finnegan, Henderson, Farabow, Garrett & Dunner, LLP

(57) ABSTRACT

An instrument access device comprises at least a first instrument seal 71 to effect a seal around a first instrument extended through the device and a second instrument seal 72 to effect a seal around a second instrument extended through the device. The instrument seals 71, 72 are configured to be arranged in a sealing relationship to a body of a patient. The device also comprises a distal anchoring ring 401 for location within a wound interior and a retractor member 402 extending proximally from the distal anchoring ring 401 to retract laterally the sides of a wound opening.

25 Claims, 34 Drawing Sheets

U.S. PATENT DOCUMENTS

| | | |
|---|---|---|
| 3,347,227 A | 10/1967 | Harrower |
| 3,397,692 A | 8/1968 | Creager, Jr. et al. |
| 3,402,710 A | 9/1968 | Paleschuck |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,656,485 A | 4/1972 | Robertson |
| 3,685,786 A | 8/1972 | Woodson |
| 3,717,151 A | 2/1973 | Collett |
| 3,729,006 A | 4/1973 | Wilder et al. |
| 3,782,370 A | 1/1974 | McDonald |
| 3,797,478 A | 3/1974 | Walsh et al. |
| 3,807,393 A | 4/1974 | McDonald |
| 3,828,764 A | 8/1974 | Jones |
| 3,841,332 A | 10/1974 | Treacle |
| 3,853,126 A | 12/1974 | Schulte |
| 3,853,127 A | 12/1974 | Spademan |
| 3,856,021 A | 12/1974 | Macintosh |
| 3,907,389 A | 9/1975 | Cox et al. |
| 3,915,171 A | 10/1975 | Shermeta |
| 3,965,890 A | 6/1976 | Gauthier |
| 3,996,623 A | 12/1976 | Kaster |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,083,370 A | 4/1978 | Taylor |
| 4,096,853 A | 6/1978 | Weigand |
| 4,130,113 A | 12/1978 | Graham |
| 4,177,814 A | 12/1979 | Knepshield |
| 4,188,945 A | 2/1980 | Wenander |
| 4,217,664 A | 8/1980 | Faso |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lehrman |
| 4,367,728 A | 1/1983 | Mutke |
| 4,399,816 A | 8/1983 | Spangler |
| 4,411,659 A | 10/1983 | Jensen et al. |
| 4,421,296 A | 12/1983 | Stephens |
| 4,424,833 A | 1/1984 | Spector |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,485,490 A | 12/1984 | Akers et al. |
| 4,488,877 A | 12/1984 | Klein |
| 4,543,088 A | 9/1985 | Bootman |
| 4,550,713 A | 11/1985 | Hyman |
| 4,553,537 A | 11/1985 | Rosenberg |
| 4,601,710 A | 7/1986 | Moll |
| 4,610,665 A | 9/1986 | Matsumuto |
| 4,626,245 A | 12/1986 | Weinstein |
| 4,634,424 A | 1/1987 | O'Boyle |
| 4,649,904 A | 3/1987 | Krauter |
| 4,654,030 A | 3/1987 | Moll et al. |
| 4,673,393 A | 6/1987 | Suzuki et al. |
| 4,673,394 A | 6/1987 | Fenton |
| 4,755,170 A | 7/1988 | Golden |
| 4,776,843 A | 10/1988 | Martinez et al. |
| 4,777,943 A | 10/1988 | Chvapil |
| 4,784,646 A | 11/1988 | Feingold |
| 4,798,594 A | 1/1989 | Hillstead |
| 4,809,679 A | 3/1989 | Shimonaka |
| 4,863,438 A | 9/1989 | Gauderer |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,015,228 A | 5/1991 | Columbus et al. |
| 5,019,101 A | 5/1991 | Purkait |
| 5,026,366 A | 6/1991 | Leckrone |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,074,878 A | 12/1991 | Bark et al. |
| 5,082,005 A | 1/1992 | Kaldany |
| 5,092,846 A | 3/1992 | Nishijima |
| 5,125,897 A | 6/1992 | Quinn et al. |
| 5,141,498 A | 8/1992 | Christian |
| 5,149,327 A | 9/1992 | Oshiyama |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,178,162 A | 1/1993 | Bose |
| 5,188,595 A | 2/1993 | Jacobi |
| 5,192,301 A | 3/1993 | Kamiya et al. |
| 5,207,656 A | 5/1993 | Kranys |
| 5,209,737 A | 5/1993 | Richartt |
| 5,211,370 A | 5/1993 | Powers |
| 5,211,633 A | 5/1993 | Strouder |
| 5,213,114 A | 5/1993 | Bailey, Jr. |
| 5,234,455 A | 8/1993 | Mulhollan |
| 5,242,409 A | 9/1993 | Buelna |
| 5,248,304 A | 9/1993 | Vigdorchik et al. |
| 5,261,883 A | 11/1993 | Hood et al. |
| 5,263,922 A | 11/1993 | Sova et al. |
| 5,269,763 A | 12/1993 | Boehmer |
| 5,269,772 A | 12/1993 | Wilk |
| D343,236 S | 1/1994 | Quigley et al. |
| 5,279,575 A | 1/1994 | Sugarbaker |
| D346,022 S | 4/1994 | Quigley et al. |
| 5,299,582 A | 4/1994 | Potts |
| 5,300,036 A | 4/1994 | Mueller |
| 5,308,336 A | 5/1994 | Hart et al. |
| 5,309,896 A | 5/1994 | Moll et al. |
| 5,316,541 A | 5/1994 | Fischer |
| 5,320,611 A | 6/1994 | Bonutti |
| 5,330,437 A | 7/1994 | Durman |
| 5,330,497 A | 7/1994 | Freitas |
| 5,334,143 A | 8/1994 | Carroll |
| 5,336,192 A | 8/1994 | Palestrant |
| 5,342,315 A | 8/1994 | Rowe et al. |
| 5,342,385 A | 8/1994 | Norelli et al. |
| 5,350,364 A | 9/1994 | Stephens et al. |
| 5,364,345 A | 11/1994 | Lowery et al. |
| 5,366,478 A | 11/1994 | Brinkerhoff et al. |
| 5,368,545 A | 11/1994 | Schaller et al. |
| 5,383,861 A | 1/1995 | Hempel |
| 5,385,553 A | 1/1995 | Hart et al. |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers |
| 5,407,433 A | 4/1995 | Loomas |
| 5,423,848 A | 6/1995 | Washizuka et al. |
| 5,429,609 A | 7/1995 | Yoon |
| 5,431,676 A | 7/1995 | Dubrul et al. |
| 5,443,452 A | 8/1995 | Hart et al. |
| 5,456,284 A | 10/1995 | Ryan |
| 5,476,475 A | 12/1995 | Gadberry |
| 5,480,410 A | 1/1996 | Cuschieri et al. |
| 5,496,280 A | 3/1996 | Vandenbroeck |
| 5,503,112 A | 4/1996 | Luhman |
| 5,514,109 A | 5/1996 | Mollenauer et al. |
| 5,514,133 A | 5/1996 | Golub et al. |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,545,179 A | 8/1996 | Williamson, IV |
| 5,562,632 A | 10/1996 | Davila |
| 5,562,688 A | 10/1996 | Riza |

| | | | |
|---|---|---|---|
| 5,577,993 A | 11/1996 | Zhu et al. | |
| 5,584,850 A | 12/1996 | Hart et al. | |
| 5,601,579 A | 2/1997 | Semertzides | |
| 5,620,415 A | 4/1997 | Lucey | |
| 5,632,979 A | 5/1997 | Goldberg | |
| 5,634,911 A | 6/1997 | Hermann et al. | |
| 5,634,936 A | 6/1997 | Linden | |
| 5,634,937 A | 6/1997 | Mollenauer et al. | |
| 5,636,645 A | 6/1997 | Ou | |
| 5,640,977 A | 6/1997 | Leahy et al. | |
| 5,649,550 A | 7/1997 | Crook | |
| 5,653,705 A | 8/1997 | de la Torre et al. | |
| 5,657,963 A | 8/1997 | Hinchliffe | |
| 5,658,272 A | 8/1997 | Hasson | |
| 5,658,306 A | 8/1997 | Kieturakis | |
| 5,672,168 A | 9/1997 | de la Torre et al. | |
| 5,685,854 A | 11/1997 | Green | |
| 5,707,703 A | 1/1998 | Rothrum et al. | |
| 5,709,664 A | 1/1998 | Vandenbroeck | |
| 5,720,730 A | 2/1998 | Blake, III | |
| 5,738,628 A | 4/1998 | Sierocuk et al. | |
| 5,741,234 A | 4/1998 | Aboul-Hosn | |
| 5,741,298 A | 4/1998 | MacLeod | |
| 5,749,882 A | 5/1998 | Hart et al. | |
| 5,755,660 A | 5/1998 | Tyagi | |
| 5,769,783 A | 6/1998 | Fowler | |
| 5,782,812 A | 7/1998 | Hart et al. | |
| 5,795,290 A | 8/1998 | Bridges | |
| 5,803,919 A | 9/1998 | Hart et al. | |
| 5,803,921 A | 9/1998 | Bonadio | |
| 5,807,350 A | 9/1998 | Diaz | |
| 5,810,721 A | 9/1998 | Mueller et al. | |
| 5,813,409 A | 9/1998 | Leahy et al. | |
| 5,814,026 A | 9/1998 | Yoon | |
| 5,817,062 A | 10/1998 | Flom | |
| 5,820,555 A | 10/1998 | Mueller | |
| 5,832,925 A | 11/1998 | Rothrum | |
| 5,853,395 A | 12/1998 | Crook et al. | |
| 5,865,728 A | 2/1999 | Moll et al. | |
| 5,871,474 A | 2/1999 | Hermann et al. | |
| 5,882,344 A | 3/1999 | Strouder | |
| 5,899,208 A | 5/1999 | Bonadio | |
| 5,904,703 A | 5/1999 | Gilson | |
| 5,906,577 A | 5/1999 | Beane et al. | |
| 5,916,232 A | 6/1999 | Hart | |
| 5,944,450 A | 8/1999 | Stevens | |
| 5,947,922 A | 9/1999 | MacLeod | |
| 5,951,467 A | 9/1999 | Picha et al. | |
| 5,957,913 A | 9/1999 | de la Torre et al. | |
| 5,964,781 A | 10/1999 | Mollenauer et al. | |
| 5,993,485 A | 11/1999 | Beckers | |
| 5,994,450 A | 11/1999 | Pearce | |
| 5,997,515 A | 12/1999 | de la Torre et al. | |
| 6,024,736 A | 2/2000 | de la Torre et al. | |
| 6,025,067 A | 2/2000 | Fay | |
| 6,033,426 A | 3/2000 | Kaji | |
| 6,033,428 A | 3/2000 | Sardella | |
| 6,036,685 A | 3/2000 | Mueller | |
| 6,042,573 A | 3/2000 | Lucey | |
| 6,048,309 A | 4/2000 | Flom et al. | |
| 6,059,816 A | 5/2000 | Moenning | |
| 6,077,288 A | 6/2000 | Shimomura et al. | |
| 6,099,506 A | 8/2000 | Macoviak et al. | |
| 6,110,154 A | 8/2000 | Shimomura et al. | |
| 6,123,689 A | 9/2000 | To | |
| 6,142,935 A | 11/2000 | Flom et al. | |
| 6,142,936 A * | 11/2000 | Beane et al. ............... 600/207 | |
| 6,150,608 A | 11/2000 | Wambeke | |
| 6,159,182 A | 12/2000 | Davis | |
| 6,162,172 A | 12/2000 | Cosgrove et al. | |
| 6,162,196 A | 12/2000 | Hart et al. | |
| 6,162,206 A | 12/2000 | Bindokas | |
| 6,163,949 A | 12/2000 | Neuenschwander | |
| 6,164,279 A | 12/2000 | Tweedle | |
| 6,171,282 B1 | 1/2001 | Ragsdale | |
| 6,183,486 B1 | 2/2001 | Snow et al. | |
| 6,238,373 B1 | 5/2001 | de la Torre et al. | |
| 6,254,533 B1 | 7/2001 | Fadem et al. | |
| 6,254,534 B1 | 7/2001 | Butler et al. | |
| 6,258,065 B1 | 7/2001 | Dennis | |
| 6,315,770 B1 | 11/2001 | de la Torre et al. | |
| 6,319,246 B1 | 11/2001 | de la Torre et al. | |
| 6,322,541 B2 | 11/2001 | West | |
| 6,346,074 B1 | 2/2002 | Roth | |
| 6,382,211 B1 | 5/2002 | Crook | |
| 6,420,475 B1 | 7/2002 | Chen | |
| 6,440,063 B1 | 8/2002 | Beane | |
| 6,450,983 B1 | 9/2002 | Rambo | |
| 6,454,783 B1 | 9/2002 | Piskun | |
| 6,458,543 B1 | 10/2002 | Gold | |
| 6,464,686 B1 | 10/2002 | O'Hara et al. | |
| 6,488,620 B1 | 12/2002 | Segermark et al. | |
| 6,533,734 B1 | 3/2003 | Corley, III et al. | |
| 6,551,270 B1 | 4/2003 | Bimbo et al. | |
| 6,554,793 B1 | 4/2003 | Pauker | |
| 6,578,577 B2 | 6/2003 | Bonadio et al. | |
| 6,582,364 B2 | 6/2003 | Butler et al. | |
| 6,589,167 B1 | 7/2003 | Shimonmura | |
| 6,589,211 B1 | 7/2003 | MacLeod | |
| 6,607,504 B2 | 8/2003 | Haarala | |
| 6,623,426 B2 | 9/2003 | Bonadio et al. | |
| 6,706,050 B1 | 3/2004 | Giannadakis | |
| 6,714,298 B2 | 3/2004 | Ryer | |
| 6,723,044 B2 | 4/2004 | Pulford | |
| 6,796,940 B2 | 9/2004 | Bonadio et al. | |
| 6,797,765 B2 | 9/2004 | Pearce | |
| 6,814,078 B2 | 11/2004 | Crook | |
| 6,814,700 B1 | 11/2004 | Mueller et al. | |
| 6,840,951 B2 | 1/2005 | de la Torre et al. | |
| 6,846,287 B2 | 1/2005 | Bonadio et al. | |
| 6,860,463 B2 | 3/2005 | Hartley | |
| 6,866,861 B1 | 3/2005 | Luhman | |
| 6,884,253 B1 | 4/2005 | McFarlane | |
| 6,902,541 B2 | 6/2005 | McNally et al. | |
| 6,908,430 B2 | 6/2005 | Caldwell | |
| 6,916,331 B2 | 7/2005 | Mollenauer et al. | |
| 6,936,037 B2 | 8/2005 | Bubb | |
| 6,939,296 B2 | 9/2005 | Ewers | |
| 6,945,932 B1 | 9/2005 | Caldwell et al. | |
| 6,958,037 B2 | 10/2005 | Ewers | |
| 6,979,324 B2 | 12/2005 | Bybordi | |
| 7,008,377 B2 | 3/2006 | Beane | |
| 7,052,454 B2 | 5/2006 | Taylor | |
| 7,081,089 B2 | 7/2006 | Bonadio et al. | |
| 7,118,528 B1 | 10/2006 | Piskun | |
| 7,195,590 B2 | 3/2007 | Butler et al. | |
| 7,300,399 B2 | 11/2007 | Bonadio et al. | |
| 7,344,547 B2 | 3/2008 | Piskun | |
| 8,613,952 | 9/2008 | Rambo | |
| 7,445,597 B2 | 11/2008 | Butler et al. | |
| 7,749,415 B2 * | 7/2010 | Brustad et al. ............... 264/102 | |
| 2001/0037053 A1 | 11/2001 | Bonadio et al. | |
| 2001/0039430 A1 | 11/2001 | Dubrul et al. | |
| 2001/0047188 A1 | 11/2001 | Bonadio et al. | |
| 2002/0002324 A1 | 1/2002 | Mcmanus | |
| 2002/0010389 A1 | 1/2002 | Butler et al. | |
| 2002/0038077 A1 | 3/2002 | de la Torre et al. | |
| 2002/0072762 A1 | 6/2002 | Bonadio et al. | |
| 2002/0111536 A1 | 8/2002 | Cuschieri et al. | |
| 2003/0028179 A1 | 2/2003 | Piskun | |
| 2003/0078478 A1 | 4/2003 | Bonadio et al. | |
| 2003/0139756 A1 | 7/2003 | Brustad | |
| 2003/0187376 A1 | 10/2003 | Rambo | |
| 2003/0192553 A1 | 10/2003 | Rambo | |
| 2003/0225392 A1 | 12/2003 | McMichael | |
| 2003/0236549 A1 | 12/2003 | Bonadio et al. | |
| 2004/0015185 A1 | 1/2004 | Ewers et al. | |
| 2004/0024363 A1 | 2/2004 | Goldberg | |
| 2004/0049100 A1 | 3/2004 | Butler | |
| 2004/0073090 A1 | 4/2004 | Butler | |
| 2004/0092795 A1 | 5/2004 | Bonadio et al. | |
| 2004/0092796 A1 | 5/2004 | Butler et al. | |
| 2004/0093018 A1 | 5/2004 | Johnson | |
| 2004/0097793 A1 | 5/2004 | Butler et al. | |
| 2004/0106942 A1 | 6/2004 | Taylor | |
| 2004/0143158 A1 | 7/2004 | Hart et al. | |
| 2004/0154624 A1 * | 8/2004 | Bonadio et al. ............... 128/849 | |
| 2004/0215063 A1 | 10/2004 | Bonadio et al. | |

| | | |
|---|---|---|
| 2004/0249248 A1 | 12/2004 | Bonadio et al. |
| 2005/0020884 A1 | 1/2005 | Heart et al. |
| 2005/0033246 A1 | 2/2005 | Ahlberg |
| 2005/0059865 A1 | 3/2005 | Kahle |
| 2005/0065543 A1 | 3/2005 | Kahle |
| 2005/0090713 A1 | 4/2005 | Gozales |
| 2005/0090716 A1 | 4/2005 | Bonadio et al. |
| 2005/0090717 A1 | 4/2005 | Bonadio et al. |
| 2005/0131349 A1 | 6/2005 | Albrecht |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0240082 A1 | 10/2005 | Bonadio et al. |
| 2005/0241647 A1 | 11/2005 | Nguyen |
| 2005/0277946 A1 | 12/2005 | Greenhalgh |
| 2005/0288558 A1 | 12/2005 | Ewers |
| 2005/0288634 A1 | 12/2005 | O'Herron |
| 2006/0020164 A1 | 1/2006 | Butler et al. |
| 2006/0020241 A1 | 1/2006 | Piskun et al. |
| 2006/0041270 A1 | 2/2006 | Lenker |
| 2006/0047284 A1 | 3/2006 | Gresham |
| 2006/0106402 A1 | 5/2006 | McLucas |
| 2006/0149306 A1 | 7/2006 | Hart et al. |
| 2006/0161050 A1 | 7/2006 | Butler et al. |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0264706 A1 | 11/2006 | Piskun |
| 2007/0004968 A1 | 1/2007 | Bonadio et al. |
| 2007/0049966 A1 | 3/2007 | Bonadio et al. |
| 2007/0093695 A1* | 4/2007 | Bonadio et al. ............ 600/208 |
| 2007/0118175 A1 | 5/2007 | Butler et al. |
| 2007/0185387 A1* | 8/2007 | Albrecht et al. ........... 600/208 |
| 2007/0203398 A1 | 8/2007 | Bonadio et al. |
| 2007/0255219 A1 | 11/2007 | Vaugh et al. |
| 2008/0027476 A1 | 1/2008 | Piskun |
| 2008/0097162 A1 | 4/2008 | Bonadio et al. |
| 2008/0097163 A1 | 4/2008 | Butler et al. |
| 2008/0255519 A1 | 10/2008 | Piskun et al. |
| 2010/0204548 A1* | 8/2010 | Bonadio et al. ............ 600/201 |

FOREIGN PATENT DOCUMENTS

| | | |
|---|---|---|
| DE | 37 37 121 | 5/1989 |
| DE | 296 00 939 | 6/1998 |
| EP | 0142262 | 5/1985 |
| EP | 0537768 | 4/1993 |
| EP | 0950376 | 10/1999 |
| EP | 1118657 | 7/2001 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1496696 | 12/1977 |
| GB | 2071502 | 9/1981 |
| GB | 2255019 | 10/1992 |
| GB | 2275420 | 8/1994 |
| JP | 10-108868 | 4/1998 |
| JP | 11-290327 | 10/1999 |
| JP | 2001-61850 | 3/2001 |
| JP | 2002-28163 | 1/2002 |
| JP | 2004-195037 | 7/2004 |
| SU | 1342485 | 1/1997 |
| WO | WO 86/06272 | 11/1986 |
| WO | WO 92/11880 | 7/1992 |
| WO | WO 92/21292 | 12/1992 |
| WO | WO 93/05740 | 4/1993 |
| WO | WO 95/05207 | 2/1995 |
| WO | WO 95/07056 | 3/1995 |
| WO | WO 95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/32514 | 9/1997 |
| WO | WO 97/32515 | 9/1997 |
| WO | WO 98/35614 | 8/1998 |
| WO | WO 98/48724 | 11/1998 |
| WO | WO 99/03416 | 1/1999 |
| WO | WO 99/25268 | 5/1999 |
| WO | WO 99/29250 | 6/1999 |
| WO | WO 00/32116 | 6/2000 |
| WO | WO 00/32117 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | WO 01/26558 | 4/2001 |
| WO | WO 01/91652 | 12/2001 |
| WO | WO 02/17800 A2 | 3/2002 |
| WO | WO 02/34108 A2 | 5/2002 |
| WO | WO 03/026512 A1 | 4/2003 |
| WO | WO 03/034908 A3 | 5/2003 |
| WO | WO 03/061480 A1 | 7/2003 |
| WO | WO 03/103548 A1 | 12/2003 |
| WO | WO 2004/026153 | 4/2004 |
| WO | WO 2004/030547 A1 | 4/2004 |
| WO | WO 2005/009257 A2 | 2/2005 |
| WO | WO 2005/034766 A2 | 4/2005 |
| WO | WO 2006/040748 A1 | 4/2006 |

OTHER PUBLICATIONS

Written Opinion for PCT/IE2008/00062 dated Oct. 21, 2008.
Kagaya, "Laparoscopic cholecystectomy via two ports, using the "Twin-Port" system", J. Hepatobiliary Pancreat Surg (2001) 8:76-80.

* cited by examiner

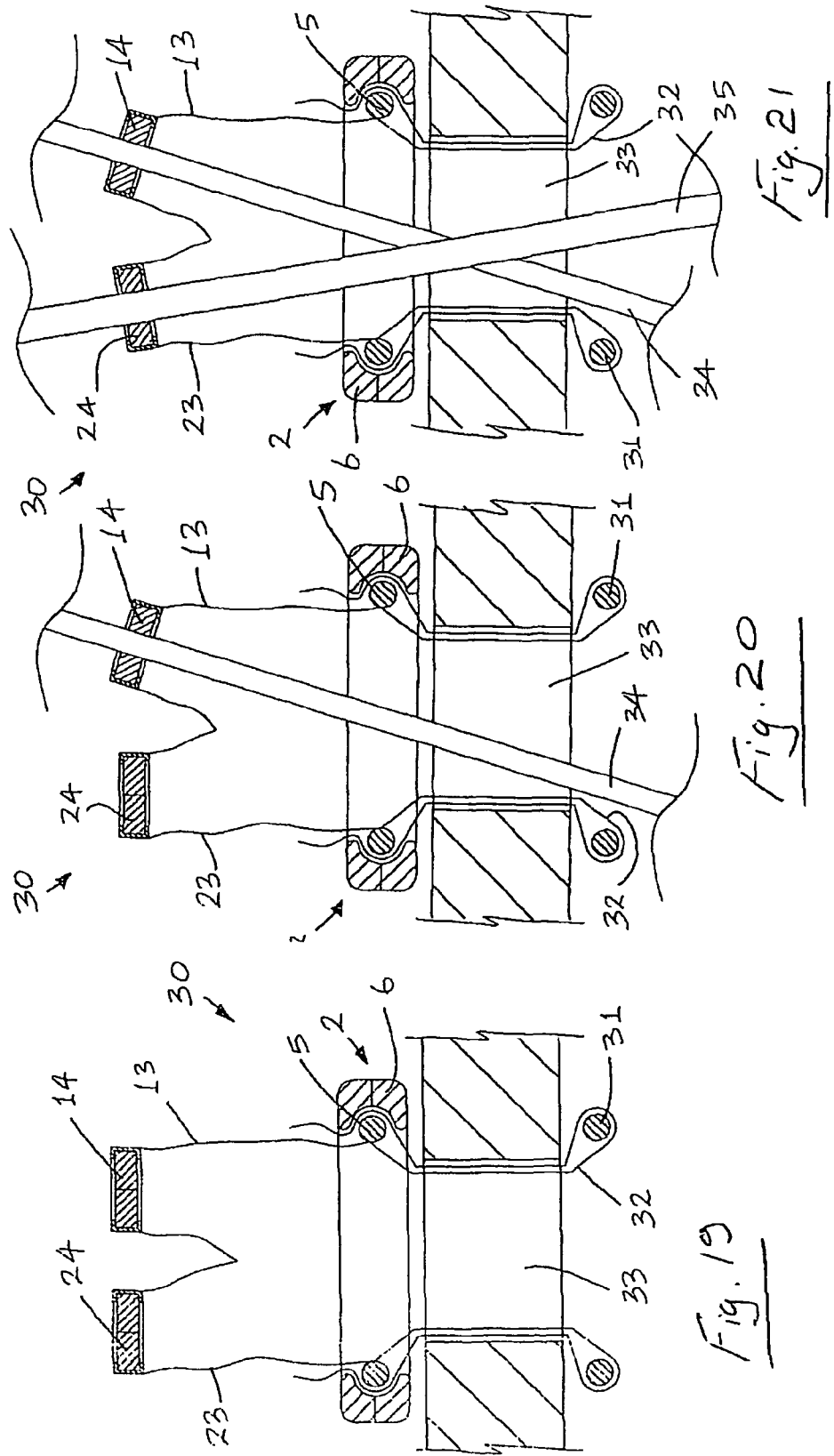

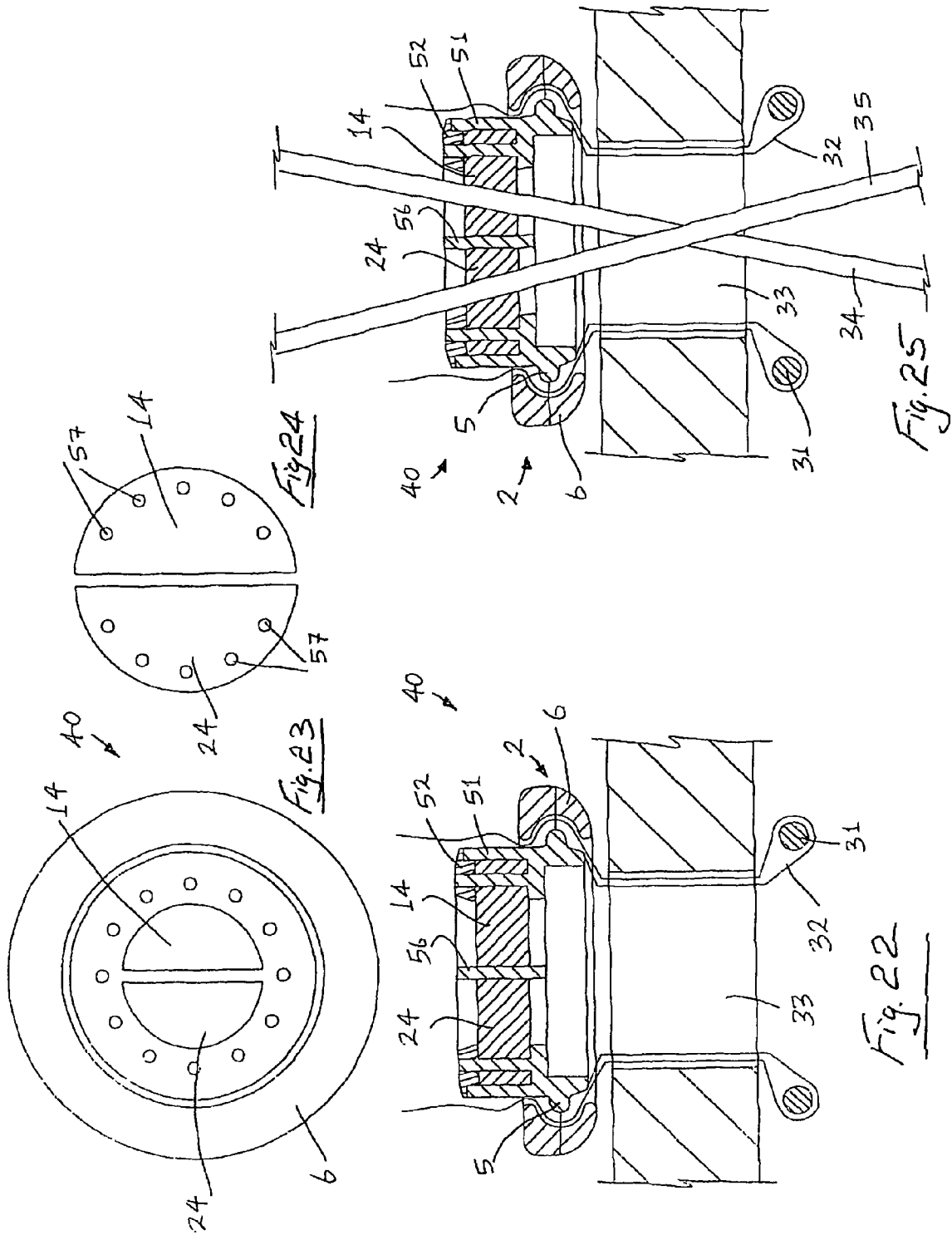

INSTRUMENT ACCESS DEVICE

This application claims the benefit of U.S. Provisional Application Nos. 60/924,918, filed Jun. 5, 2007; 60/935,625, filed Aug. 22, 2007; and 60/996,760, filed Dec. 4, 2007. The content of these provisional applications are incorporated herein by reference.

INTRODUCTION

This invention relates to an instrument access device. This invention also relates to a method of performing a surgical procedure. In one embodiment this invention relates to a method of performing a laparoscopic cholecystectomy procedure.

STATEMENTS OF INVENTION

The device of the invention comprises at least one instrument seal to effect a seal around at least one instrument extended through the device, the instrument seal being configured to be arranged in sealing relationship to a body of a patient. The device preferably has a distal anchoring member for location within a wound interior. The device preferably also has a retractor member extending proximally from the distal anchoring member to retract laterally the sides of a wound opening. Preferably the device comprises a first instrument seal to effect a seal around a first instrument extended through the device, and a second instrument seal to effect a seal around a second instrument extended through the device. By providing the two seal arrangement, this ensures that insertion or manipulation or removal of the second instrument does not adversely effect the seal around the first instrument. The device may comprise a third instrument seal to effect a seal around a third instrument extended through the device. The first instrument seal may be spaced apart from the second instrument seal. The first instrument seal may be formed separately from the second instrument seal. The first instrument seal may have a larger radial dimension than the second instrument seal. The instrument seal may be of a gelatinous elastomeric material.

In one case the device comprises a proximal member for location externally of a wound opening. The retractor member may extend at least between the distal anchoring member and the proximal member. The retractor member may extend in two layers between the distal anchoring member and the proximal member. A first end portion of the retractor member may be fixed to the proximal member. The retractor member may be movable relative to the distal anchoring member. A second end portion of the retractor member may be movable relative to the proximal member. The retractor member may extend distally from the proximal member to the distal anchoring member, may be looped around the distal anchoring member, and may extend proximally from the distal anchoring member to the proximal member. The proximal member may comprise an inner part and an outer part. The retractor member may extend between the inner part and the outer part.

In another embodiment the instrument seal is spaced proximally of the proximal member. The device may comprise at least one connector member to connect the proximal member to the at least one instrument seal. The connector member facilitates a degree of lateral movement of the instrument while maintaining the seal. The connector member may comprise a sleeve. The connector member may be of a laterally flexible material. The connector member may be of a longitudinally rigid material. The connector member may be of a rubber-like material. The connector member may be of a longitudinally flexible material.

In another case the instrument seal is mounted to the connector member. The instrument seal may be releasably mounted to the connector member. The instrument seal may comprise a mounting part to mount the instrument seal to the connector member. The mounting part may be of a rigid material. The instrument seal may comprise a sealing part to effect a seal around an instrument extended through the device, the sealing part being overmoulded over at least part of the mounting part.

In one embodiment the connector member is mounted to the proximal member. The connector member may be releasably mounted to the proximal member. The connector member may be mounted to the proximal member in an interference fit arrangement. The connector member may be mounted to the proximal member in a snap-fit arrangement. The connector member may comprise at least one protrusion for engagement with the proximal member. The protrusion can be resilient. The device may comprise a clamp member to clamp the connector member to the proximal member. The connector member may be inclined relative to the proximal member. The device may comprise a reinforcement element to reinforce the connector member. The reinforcement element may be of a rigid material. The reinforcement element may be embedded within the connector member.

The invention also provides a method of performing a surgical procedure utilising the device of the invention.

According to the invention there is provided a method of performing a surgical procedure comprising the steps of:
providing an instrument access device comprising at least one instrument seal, a distal anchoring member, and a retractor member extending proximally from the distal anchoring member;
inserting the distal anchoring member within the wound interior;
retracting laterally the sides of the wound opening using the retracting member;
inserting one or more surgical instruments through the instrument seal into the wound opening;
severing one or more body parts in the wound interior; and
removing the one or more body parts through the wound opening.

In one embodiment of the invention the method comprises the step of creating the wound opening. The wound opening may be created by creating a skin incision, and subsequently forcing tissue apart. The wound opening may be created using a Hasson cut-down incision.

In one case the method comprises the step of inserting an instrument access device at least partially through the wound opening. The instrument access device may be inserted at least partially through the wound opening using an introducer device. The method may comprise the step of inserting at least part of the instrument access device into the introducer device. The method may comprise the step of inserting the introducer device at least partially through the wound opening. The method may comprise the step of ejecting at least part of the instrument access device from the introducer device within the wound interior. The method may comprise the step of removing the introducer device from the wound opening.

In another embodiment the method comprises the step of retracting the wound opening.

In another case the method comprises the step of insufflating the wound interior.

In one embodiment the one or more surgical instruments are inserted through the instrument access device. The one or more body parts may be removed through the instrument access device. The one or more body parts may be removed through one or more seal members of the instrument access device. The method may comprise the step of detaching one or more seal members of the instrument access device from a retractor member of the instrument access device. The one or more body parts may be removed through the retractor member.

The surgical instrument may comprise a shaft having at least one bend in the shaft. The bend may be a fixed bend. The surgical instrument may comprise a shaft and an end effector at a distal end of the shaft. The end effector may be rotatable relative to the shaft.

In one case the method comprises a method of performing a laparoscopic surgical procedure. In another case the method comprises a method of performing a cholecystectomy procedure.

BRIEF DESCRIPTION OF THE DRAWINGS

The invention will be more clearly understood from the following description of some embodiments thereof, given by way of example only, with reference to the accompanying drawings, in which:—

FIGS. 19 to 21 are views similar to FIG. 3 of another instrument access device according to the invention, in use;

FIG. 22 is a view similar to FIG. 3 of another instrument access device according to the invention;

FIG. 23 is a plan view of the instrument access device of FIG. 22;

FIG. 24 is a plan view of part of the instrument access device of FIG. 22;

FIG. 25 is a view similar to FIG. 3 of the instrument access device of FIG. 22, in use;

DETAILED DESCRIPTION

Figure 1:
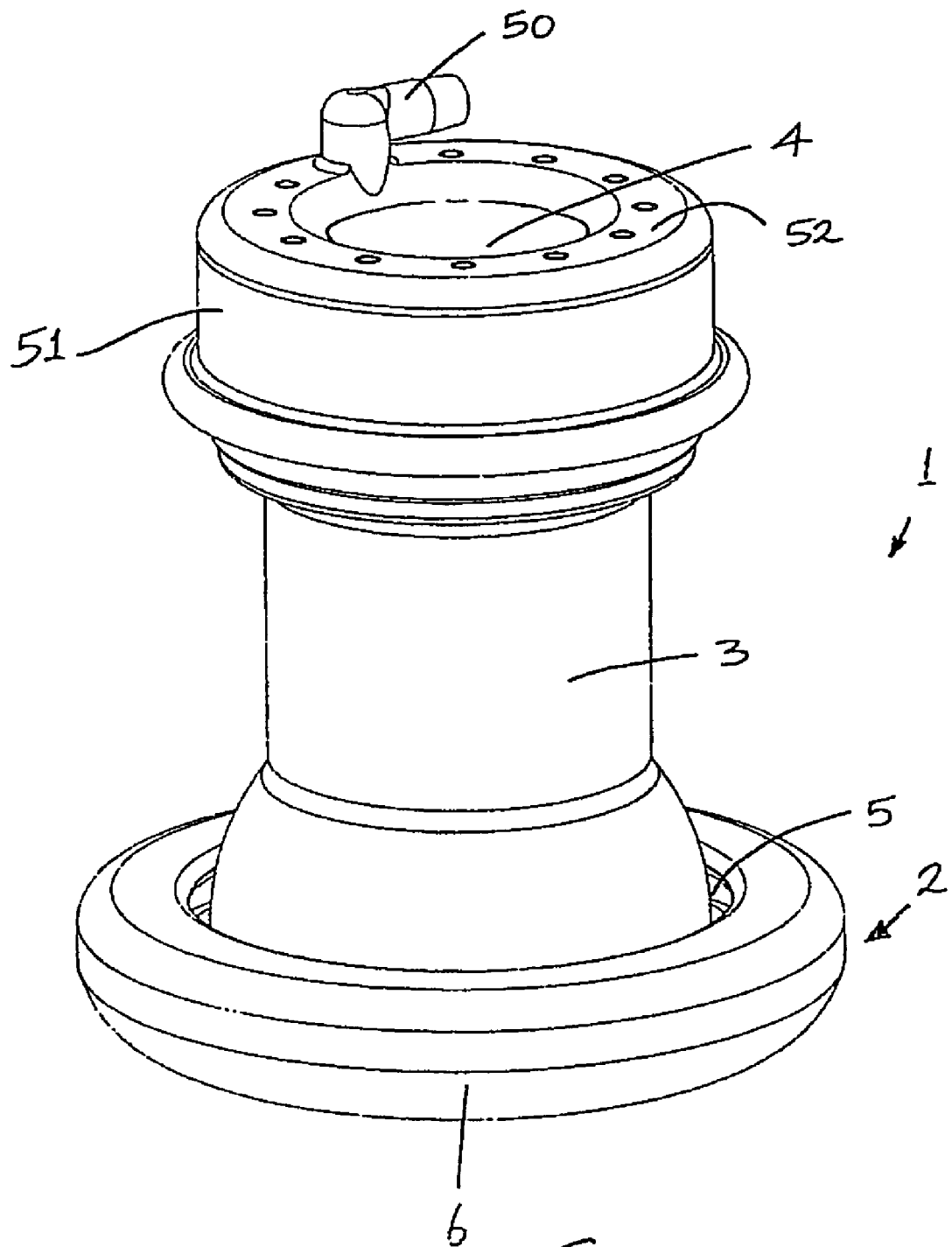
FIG. 1 is an isometric view of an instrument access device according to the invention.
Figure 3:
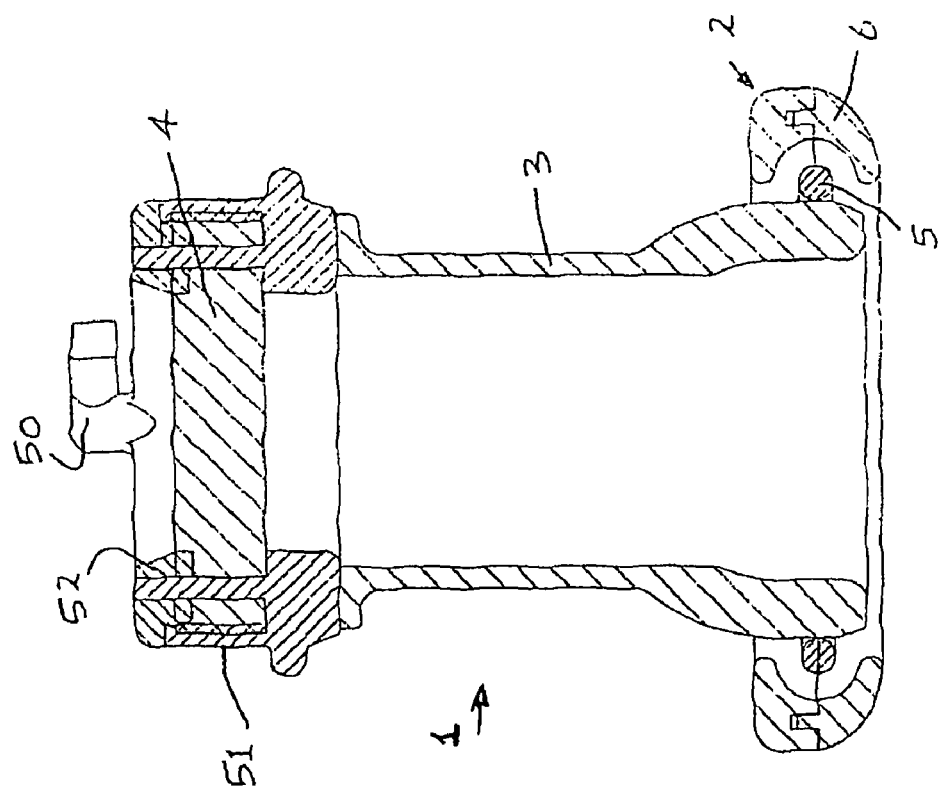
FIG. 3 is a cross-sectional, side view of the instrument access device of FIG. 1.
Figure 2:
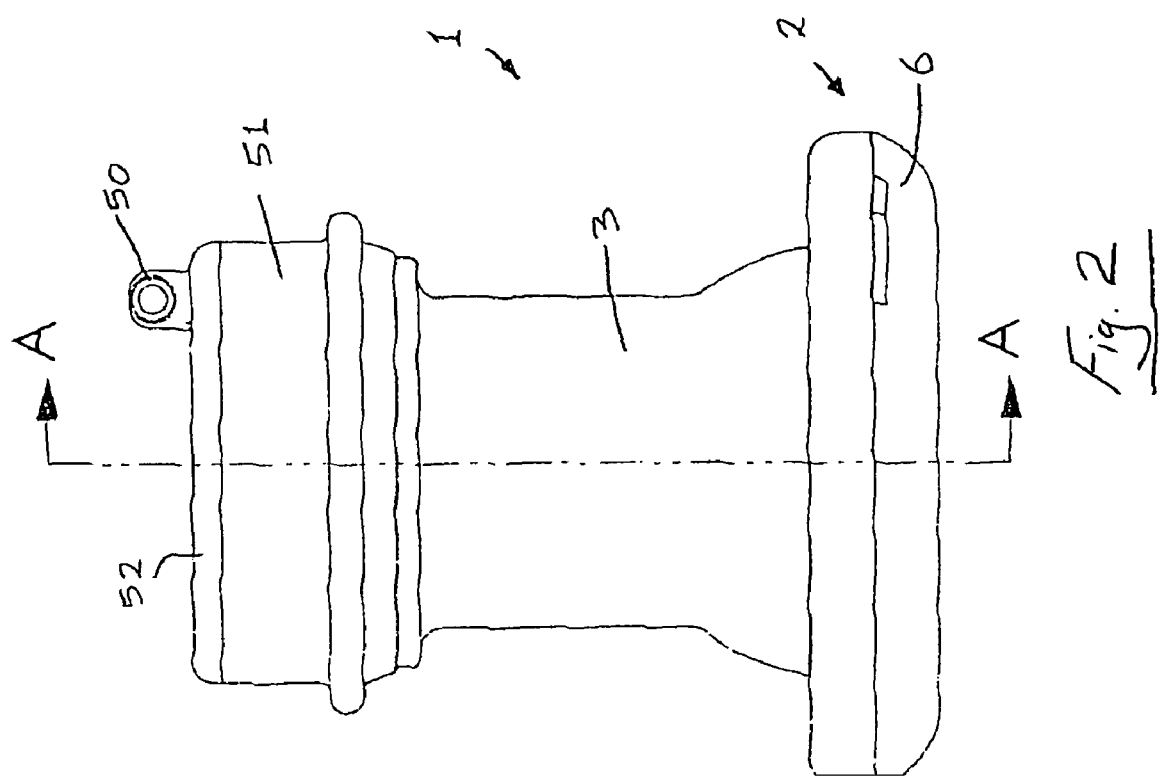
FIG. 2 is a side view of the instrument access device of FIG. 1.

Referring to the drawings, and initially to FIGS. 1 to 3 thereof, there is illustrated an instrument access device 1 according to the invention. The device 1 is suitable for use during laparoscopic surgery to facilitate instrument access to an insufflated abdominal cavity while maintaining pneumoperitoneum.

The device 1 comprises a distal anchoring ring, a retractor member, a proximal ring assembly 2, a connector sleeve 3, and an instrument seal 4. The distal anchoring ring and the retractor member are not illustrated in FIGS. 1 to 3. One such retractor is described in our US 2005-0090717 A, the entire contents of which are incorporated herein by reference.

The distal anchoring ring is located within a wound interior, in use. In this case the distal anchoring ring is provided in the form of an O-ring.

The proximal ring assembly 2 is located externally of a wound opening, in use. The proximal ring assembly 2 comprises an inner ring part 5 and an outer ring part 6. In this case the inner ring part 5 is provided in the form of an O-ring.

The retractor member may be employed to retract laterally the sides of a wound opening. The retractor member extends between the distal anchoring ring and the proximal ring assembly 2 in two layers. A first end of the retractor member is fixed to the inner ring part 5. The retractor member extends distally from the inner ring part 5 to the distal anchoring ring, is looped around the distal anchoring ring, extends proximally from the distal anchoring ring to the proximal ring assembly 2, and extends proximally between the inner ring part 5 and the outer ring part 6. The retractor member is slidably movable relative to the distal anchoring ring, and a second end of the retractor member is slidably movable between the inner ring part 5 and the outer ring part 6.

In this case the retractor member is provided in the form of a sleeve.

The instrument seal 4 may be employed to effect a seal around an instrument extended through the device 1. The instrument seal 4 is arranged in sealing relationship to a body of a patient, in use. The instrument seal 4 is spaced proximally of the proximal ring assembly 2. In this case the instrument seal 4 is of a gelatinous elastomeric material.

The connector sleeve 3 connects the proximal ring assembly 2 to the instrument seal 4. The connector sleeve 3 is of a laterally flexible and longitudinally rigid material. In this case the connector sleeve 3 is of a rubber-like material, such as polyurethane.

FIG. 1 illustrates the offset port 1 with the rubber tube 3. FIG. 1 illustrates an insufflation port 50, a gel housing 51, a gel cap 52, the rubber offset tube 3, the outer proximal ring 6, and the proximal 'O' ring 5. FIG. 2 illustrates the offset port 1 with the rubber tube 3, the insufflation port 50, and the outer proximal ring 6. FIG. 3 illustrates the gelatinous instrument seal 4, the gel housing 51, the proximal 'O' ring 5, and the rubber offset tube 3 which is flexible enough to allow full range of motion for an instrument. The structural rigidity in the rubber offset tube wall 3 allows an instrument to be passed through the valve 1 without support from the surgeon's other hand.

In use, a wound opening is created in a tissue wall, and the distal anchoring ring is inserted through the wound opening into the wound interior. The proximal ring assembly 2 is located externally of the wound opening, with the retractor member extending proximally from the distal anchoring member through the wound opening. The second end of the retractor member is pulled proximally relative to the proximal ring assembly 2 to retract laterally the sides of the wound opening. An instrument may then be inserted through the instrument seal 4, extended through the connector sleeve 3, extended through the retracted wound opening and into the wound interior.

Figure 4:
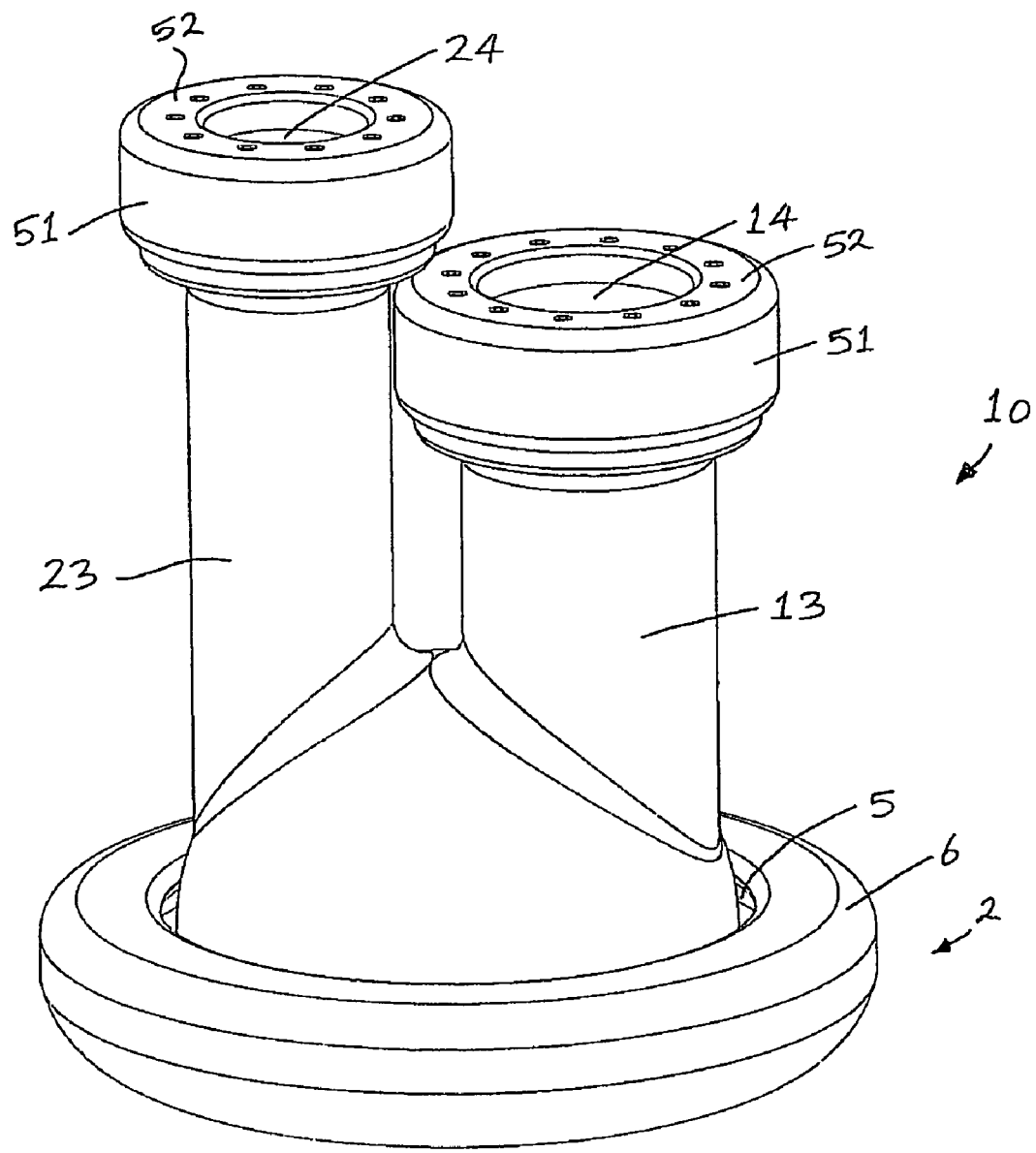
FIGS. 4 and 5 are views similar to FIGS. 1 and 2 of another instrument access device according to the invention.
Figure 5:
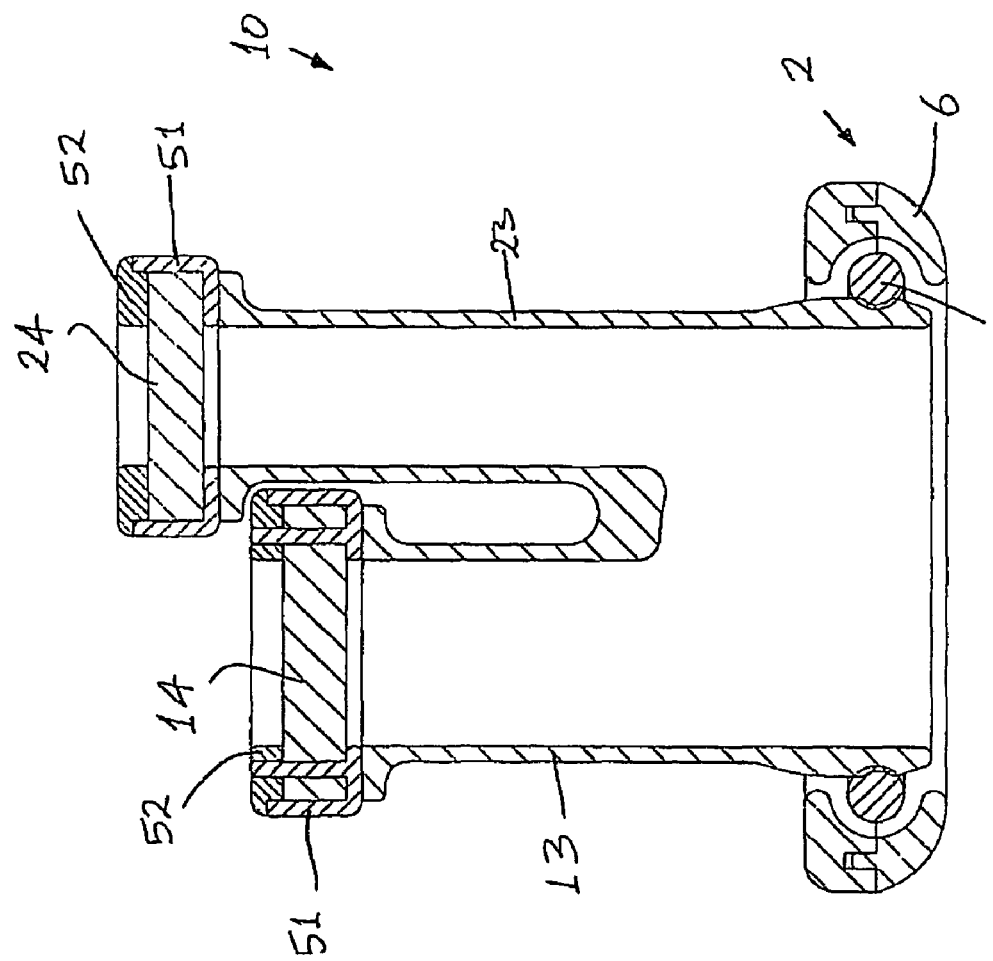

In FIGS. 4 and 5 there is illustrated another instrument access device 10 according to the invention, which is similar to the instrument access device 1 of FIGS. 1 to 3, and similar elements in FIGS. 4 and 5 are assigned the same reference numerals.

In this case the device 10 comprises a first instrument seal 14, a second instrument seal 24, a first connector sleeve 13 and a second connector sleeve 23.

The first instrument seal 14 may be employed to effect a seal around a first instrument extended through the device 10. Similarly the second instrument seal 24 may be employed to effect a seal around a second instrument extended through the device 10. The first instrument seal 14 is formed separately from the second instrument seal 24, and is spaced apart from the second instrument seal 24. The first instrument seal 14 has a larger diameter than the second instrument seal 24.

The first connector sleeve 13 connects the proximal ring assembly 2 to the first instrument seal 14. Similarly the second connector sleeve 23 connects the proximal ring assembly 2 to the second instrument sleeve 24.

FIG. 4 illustrates the double offset port 10. The ports 14, 24 may be for 5 mm or 10 mm or other sized instruments. FIG. 4 illustrates the gel 24, e.g. 5 mm port, the gel 14, e.g. 10 mm port, the outer proximal ring 6, and the rubber offset components 13, 23, which are flexible to allow full range of instrument motion. The structural rigidity of the rubber offset component legs 13, 23 allow the surgeon to pass instruments through the ports 14, 24 without needing to support it with his other hand.

FIG. 5 illustrates the double offset port 10, the gel caps 52, the gels 14, 24, the gel housings 51, the rubber offset components 13, 23, the proximal 'O' ring 5, and the outer proximal ring 6.

Referring to FIGS. 6 to 10 there is illustrated another instrument access device 70 according to the invention, which is similar to the instrument access device 10 of FIGS. 4 and 5, and similar elements in FIGS. 6 to 10 are assigned the same reference numerals. In this case a retractor 400 is illustrated and comprises a distal anchoring ring in the form of an O-ring 401. A retractor member comprises a sleeve 402 which in this case extends in two layers between the distal anchoring ring 401 and the proximal ring assembly 2.

In this case the device 70 comprises a first instrument seal 71, a second instrument seal 72, a third instrument seal 73, a first connector sleeve 74, a second connector sleeve 75, and a third connector sleeve 76.

Each instrument seal 71, 72, 73 may be employed to effect a seal around a separate instrument extended through the device 70. Each instrument seal 71, 72, 73 is formed separately from the other instrument seals 71, 72, 73, and is spaced apart from the other instrument seals 71, 72, 73. The first instrument seal 71 has a diameter equal to the diameter of the second instrument seal 72. The third instrument seal 73 has a larger diameter than the second instrument seal 72.

Each connector sleeve 74, 75, 76 connects the proximal ring assembly 2 to one of the instrument seals 71, 72, 73.

Each instrument seal 71, 72, 73 comprises a sealing part 77 of a gelatinous elastomeric material, and a mounting part 78 of a rigid material. The sealing part 77 effects a seal around an instrument extended through the device 70. The mounting part 78 facilitates releasable mounting of the instrument seal 71, 72, 73 to the connector sleeve 74, 75, 76 in a gas-tight manner. The mounting part 78 comprises an outwardly protruding barb 79 for an interference fit between the mounting part 78 and the connector sleeve 74, 75, 76. The sealing part 77 is overmoulded over part of the mounting part 78 to connect the sealing part 77 to the mounting part 78.

The device 70 comprises a connector base 80 to releasably mount the connector sleeves 74, 75, 76 to the inner ring part 5 in a gas-tight manner. The base 80 comprises outwardly protruding ridges 81 for an interference fit between the base 80 and the inner ring part 5.

A rigid reinforcement ring 82 is embedded within the base 80 to reinforce the base 80.

Figure 7:
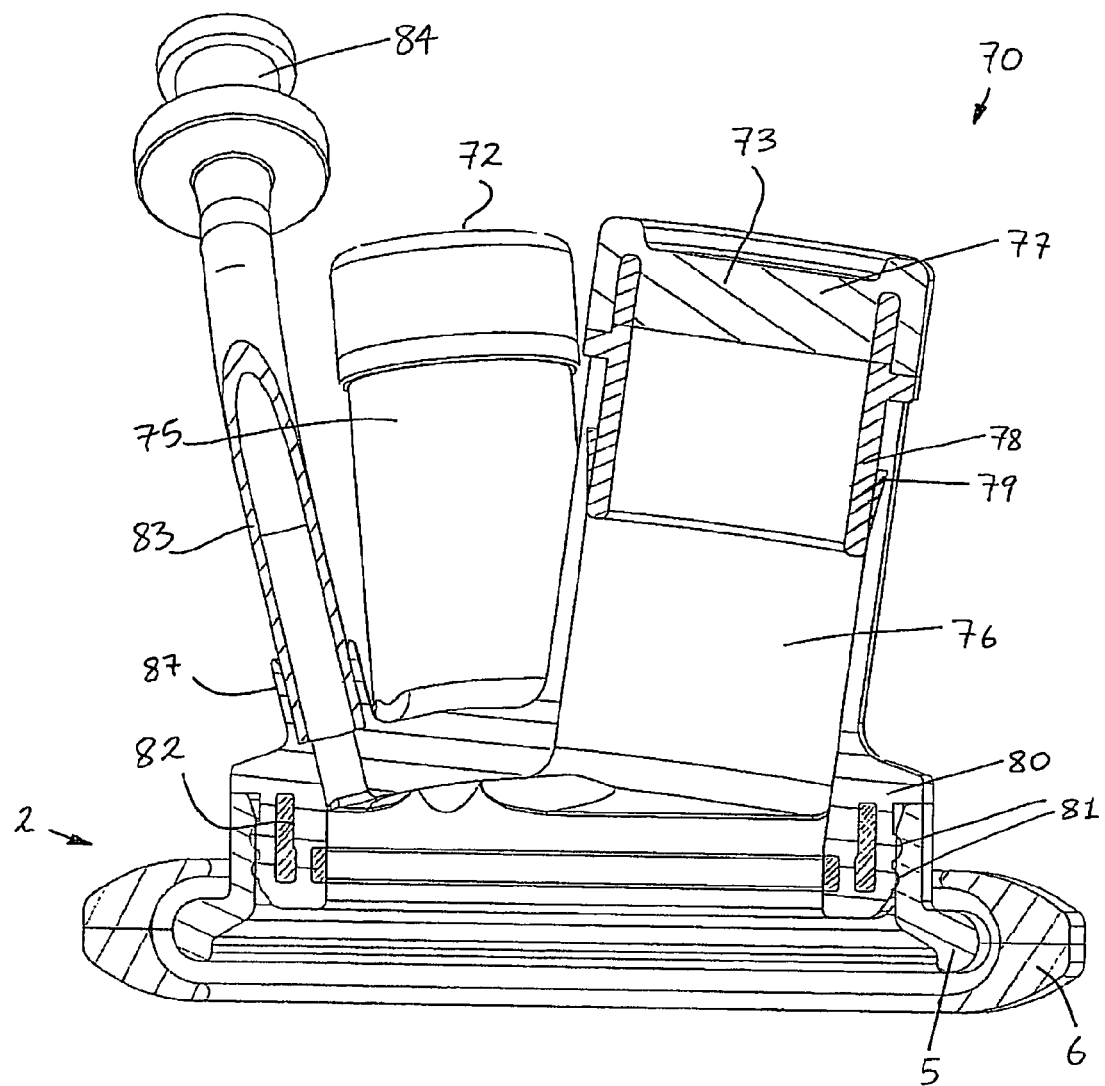

Each connector sleeve 74, 75, 76 is inclined relative to the proximal ring assembly 2 (FIG. 7).

Figure 6:
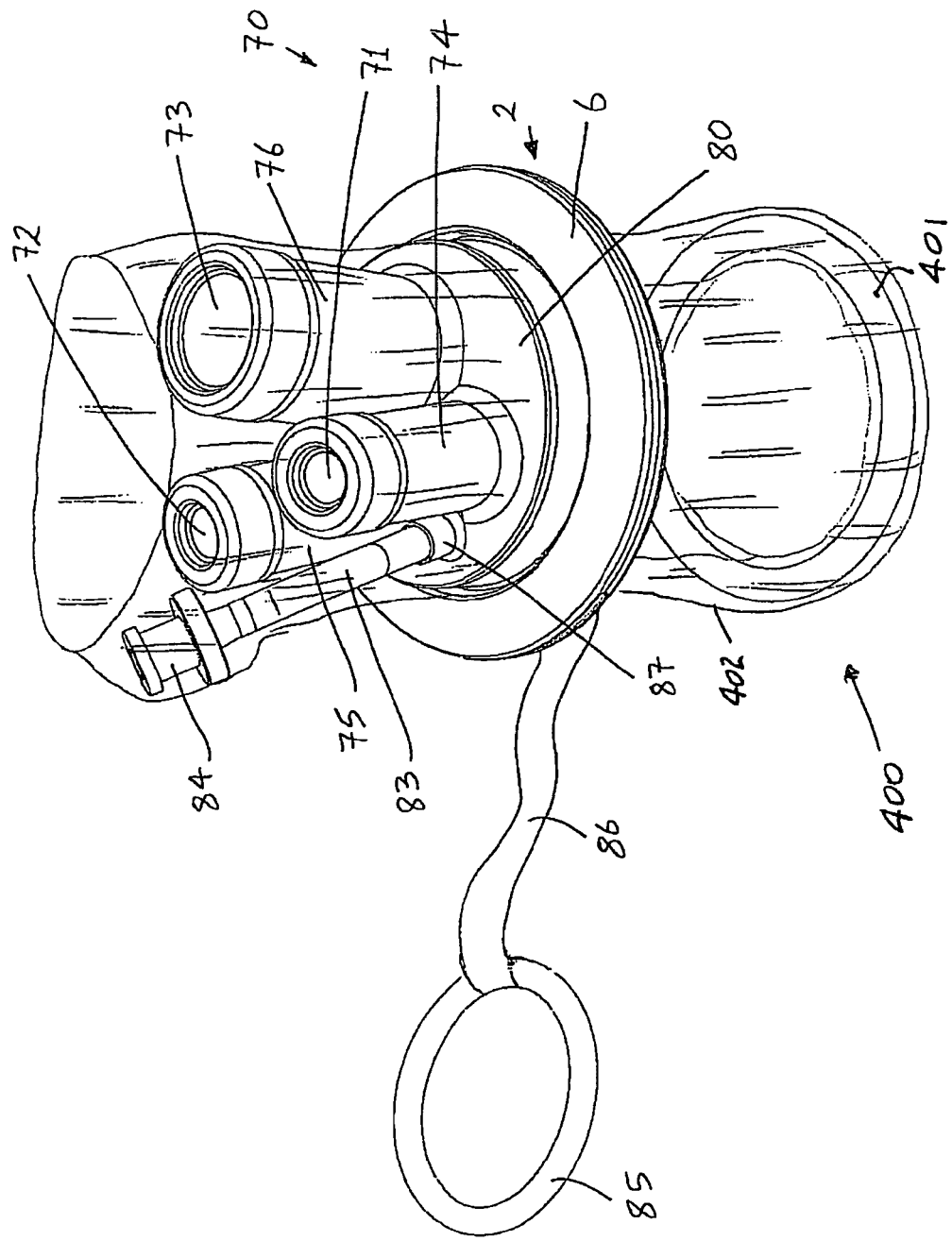
FIGS. 6 and 7 are views similar to FIGS. 1 and 3 of another instrument access device according to the invention.

FIG. 6 illustrates an insufflation line 83, a luer connection 84, the 5 mm gel port 72, the 12 mm gel port 73, a removal ring 85, a removal ribbon 86, the 5 mm gel port 71, the outer proximal ring 6, an insufflation cup 87, the 5 mm rubber leg 74, and the 12 mm rubber leg 76.

FIG. 7 illustrates the luer connector 84, the insufflation line 83, the 5 mm leg 75, the insufflation cup 87, the gas seal 81, the outer proximal ring 6, the overmould support ring 82 for the triport boot 80, the 5 mm overmoulded gel 72, the 5 mm overmould tube 75, the 12 mm overmould gel 73, the 12 mm overmould tube 78, the interference fit between the barb 79 on the overmould tube 78 and the rubber 12 mm leg 76, the triport boot 80, the inner proximal ring 5.

Figure 8:
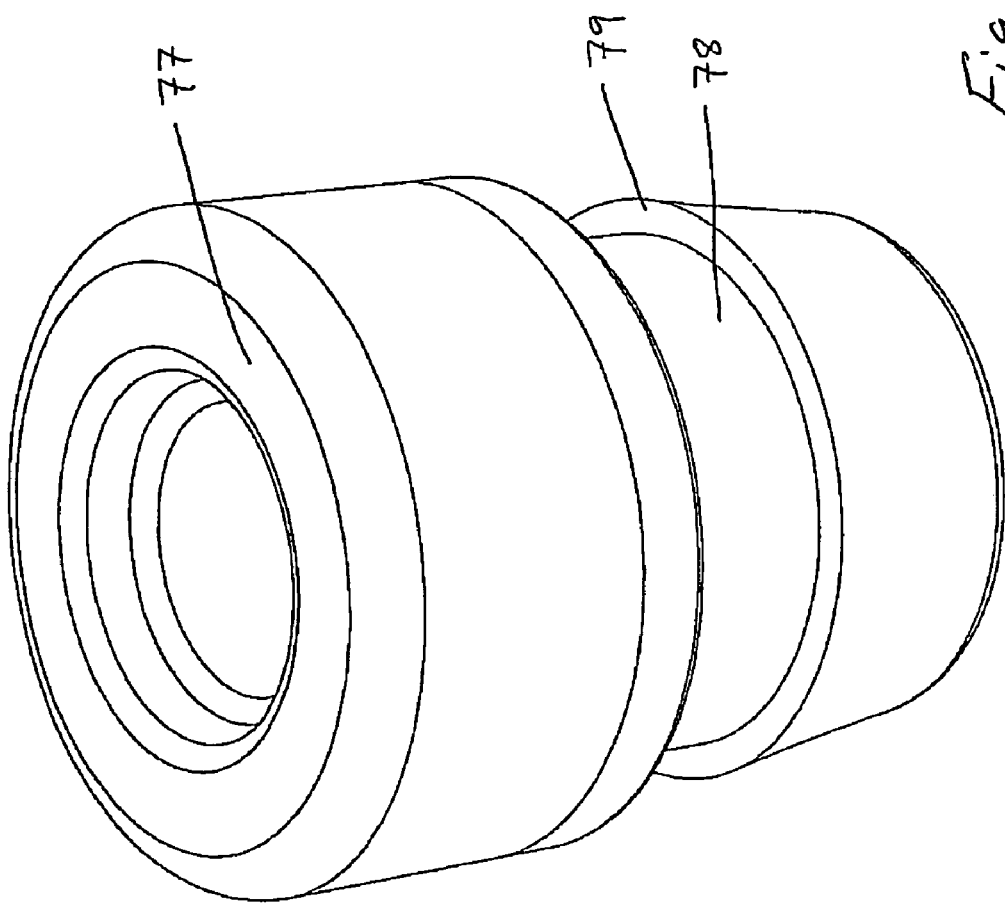
FIG. 8 is an isometric view of an instrument seal of the instrument access device of FIGS. 6 and 7.

FIG. 8 illustrates the 5 mm gel 77 overmoulded onto the 5 mm overmould tube 78, with the barb section 79.

Figure 9:
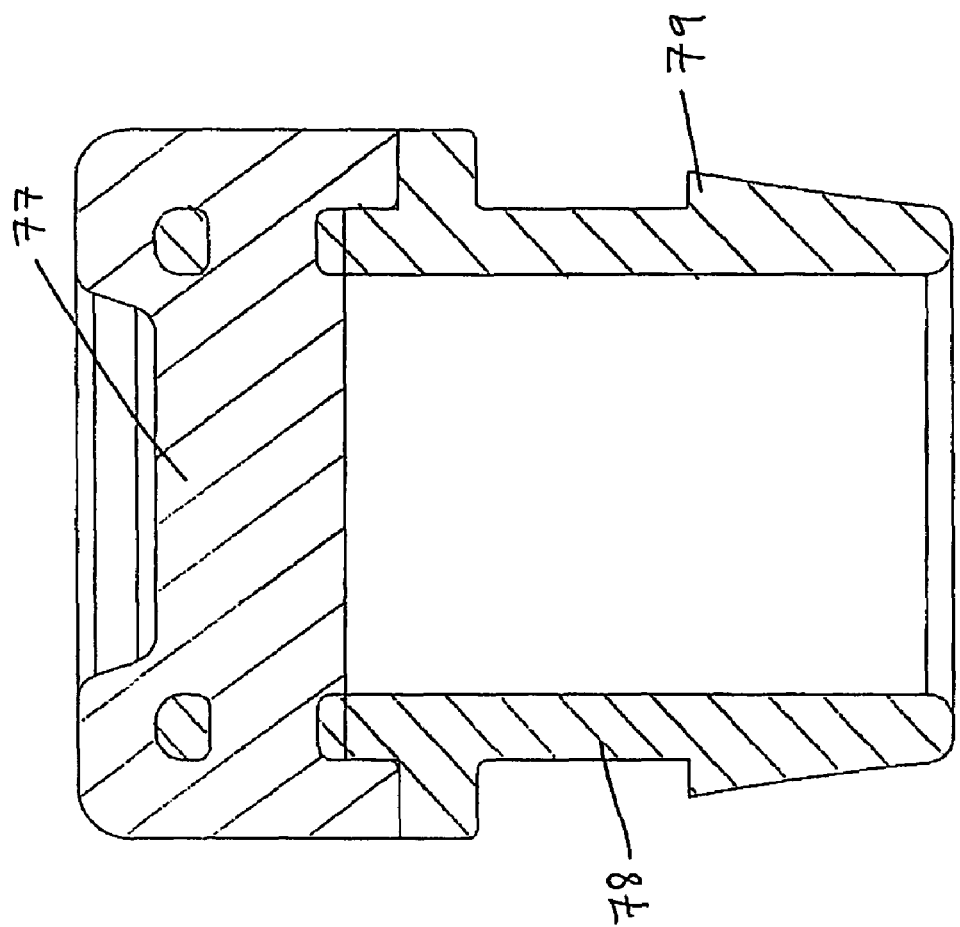
FIG. 9 is a cross-sectional, side view of the instrument seal of FIG. 8.

FIG. 9 illustrates the 5 mm gel 77 overmoulded onto the 5 mm overmould tube 78.

Figure 10:
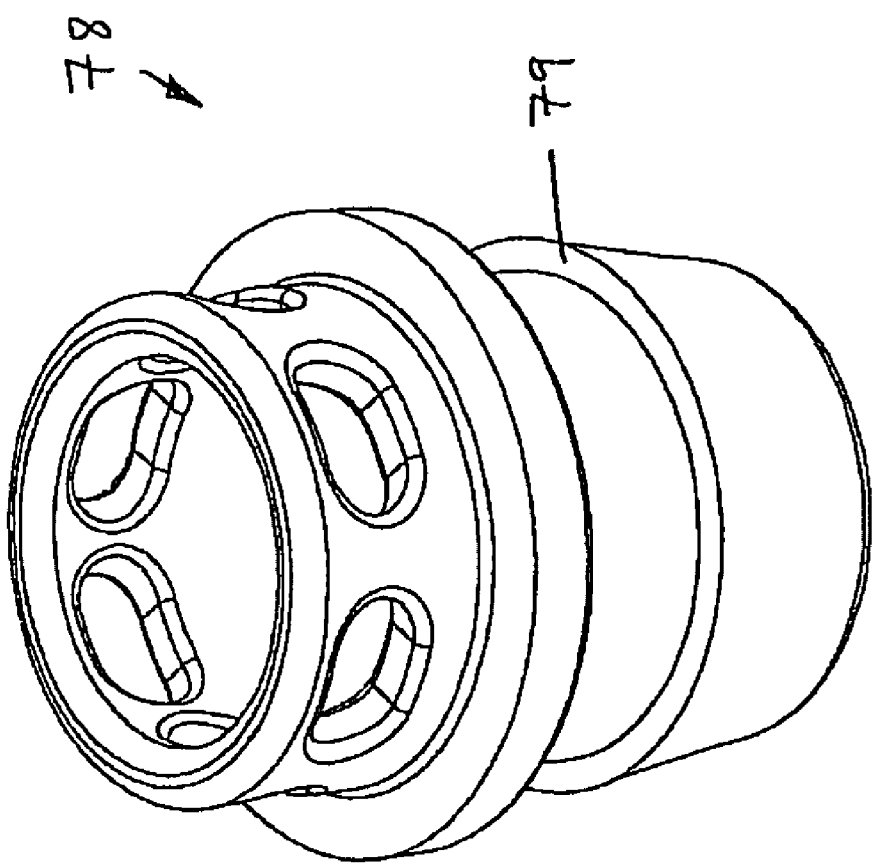
FIG. 10 is an isometric view of a mounting part of the instrument access device of FIGS. 6 and 7.

FIG. 10 illustrates the 5 mm gel overmould tube 78 with the barb 79 for the interference fit on the 5 mm rubber leg 74.

Figure 11:
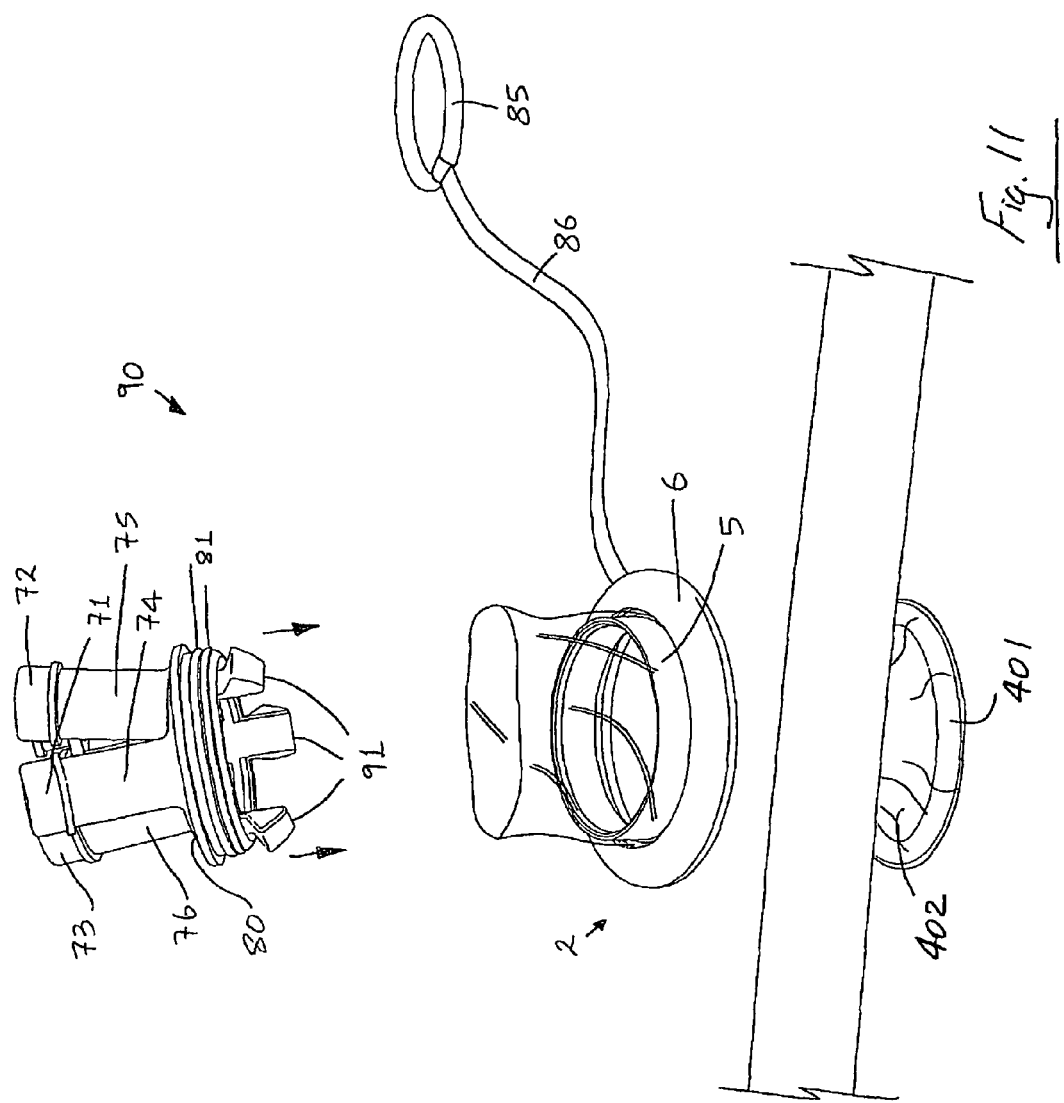
FIG. 11 is an isometric view of another instrument access device according to the invention.
Figure 12:
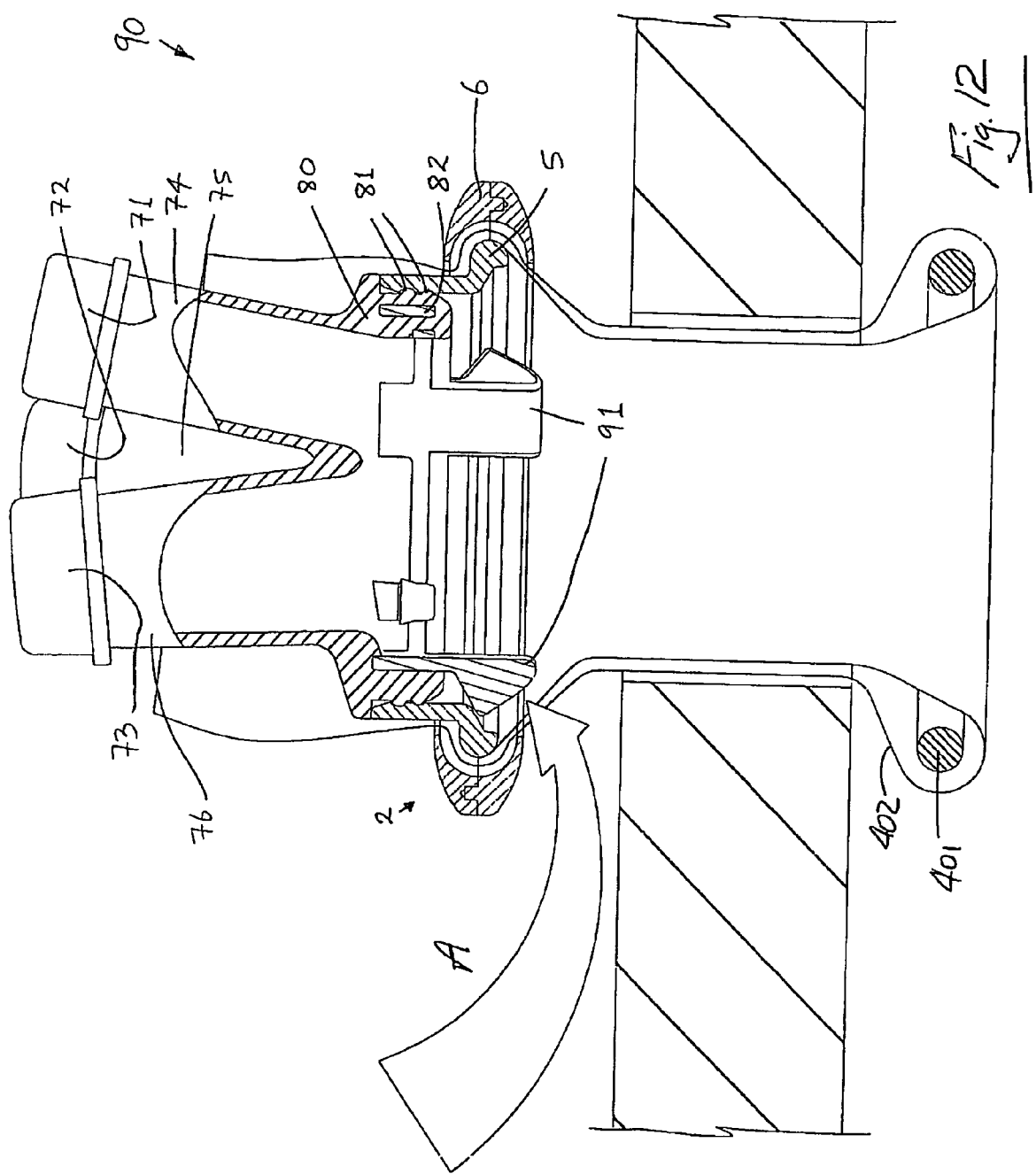
FIG. 12 is a cross-sectional, side view of the instrument access device of FIG. 11.

In FIGS. 11 and 12 there is illustrated another instrument access device 90 according to the invention, which is similar to the instrument access device 70 of FIGS. 6 to 10, and similar elements in FIGS. 11 and 12 are assigned the same reference numerals.

In this case the connector base 80 comprises three resilient finger protrusions 91 which are engagable with the inner ring part 5 for a snap-fit mounting of the connector base 80 to the inner ring part 5.

FIG. 12 illustrates that a surgeon may reach under the outer proximal ring 6 and press on the clip 91 using an arrow A with a finger to release the connector base 80.

Figure 13:
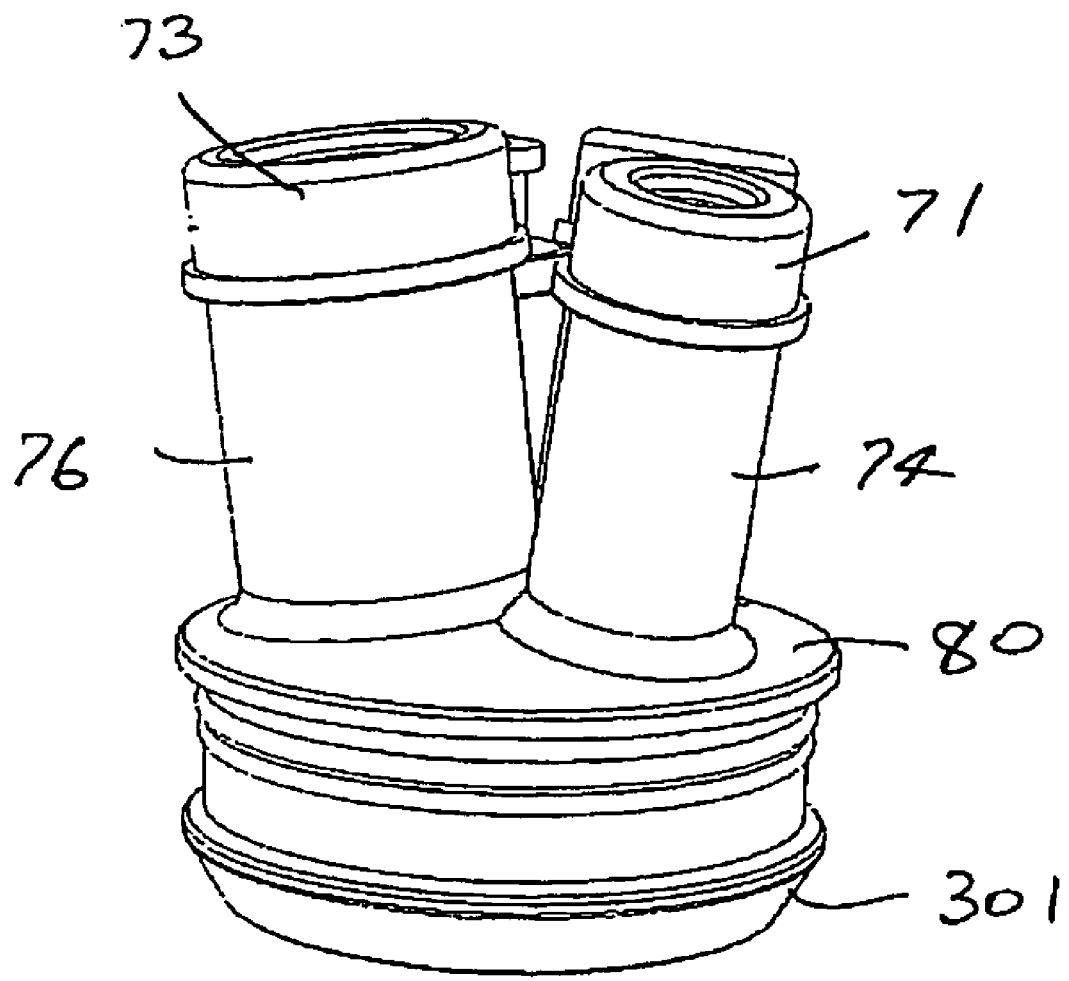
FIGS. 13 and 14 are respectively isometric and cross sectional views of another instrument access device of the invention.
Figure 14:
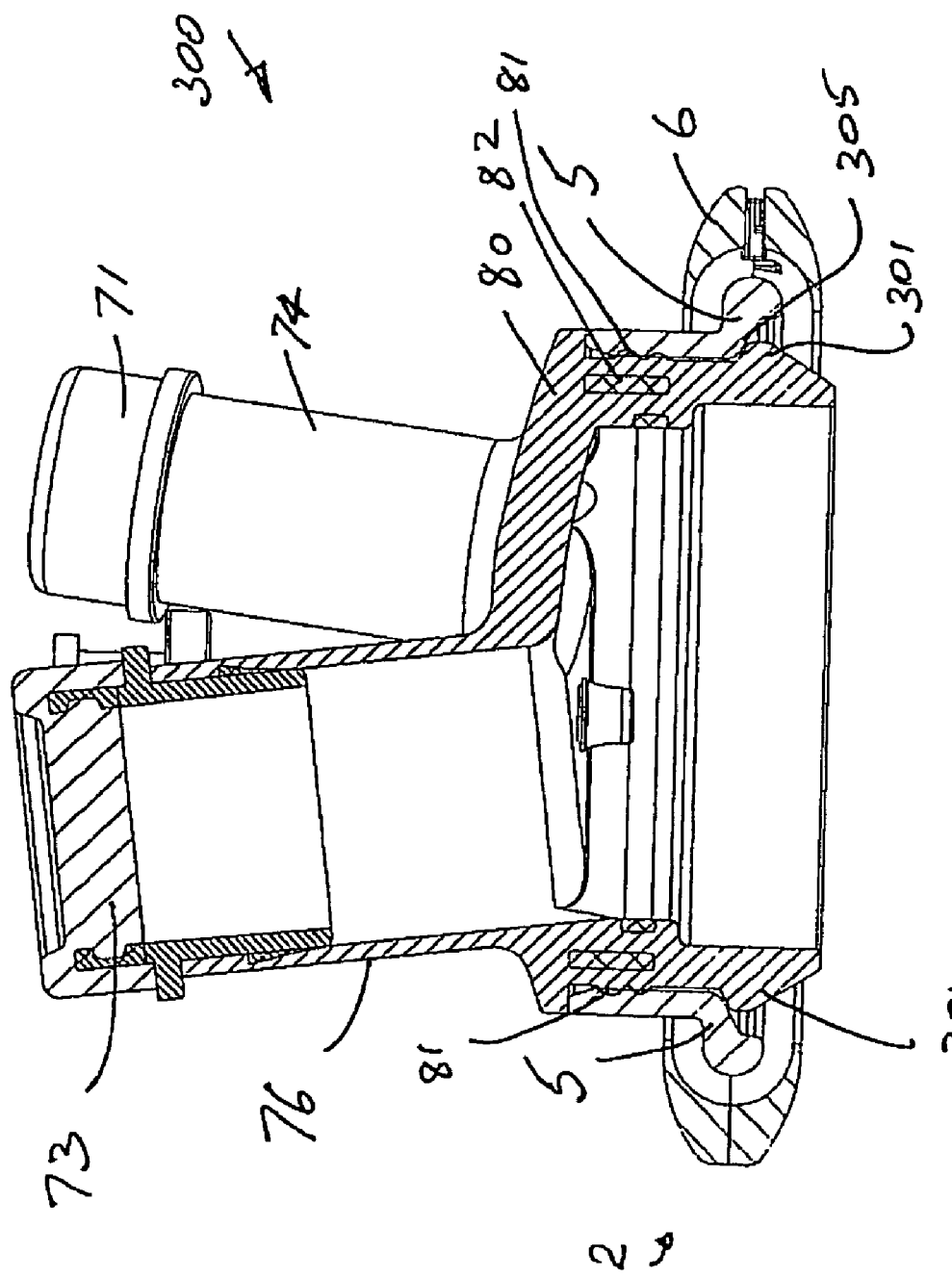

Referring to FIGS. 13 and 14 there is illustrated another instrument access device 300 according to the invention, which is similar to the instrument access device 90 of FIGS. 11 and 12, and similar elements in FIGS. 13 and 14 are assigned the same reference numerals.

In this case the connector base 80 of the device comprises an extended skirt attachment means provided by a ring 301 having a circumferentially extending protrusion 302 which is engagable with the inner ring part 5 for monitoring of the connector base 80 to the inner ring part 5. The ring 301 is of a shape that engages with an undercut surface 305 of the proximal ring. The advantages of this arrangement include ease of manufacture as the ring 301 is integral with the base 80. The engagement of the protrusion 302 with the undercut surface 305 provides a particularly secure attachment that allows instruments to be manipulated within the device. Because the protrusion 302 extends circumferentially fully around the ring, a surgeon can readily engage the ring 301 and push it out of engagement with the inner ring part 5. In this way the base 80 may be disengaged and removed if, for example, the surgeon wishes to remove a large piece of tissue, organ or body part.

Figure 15:
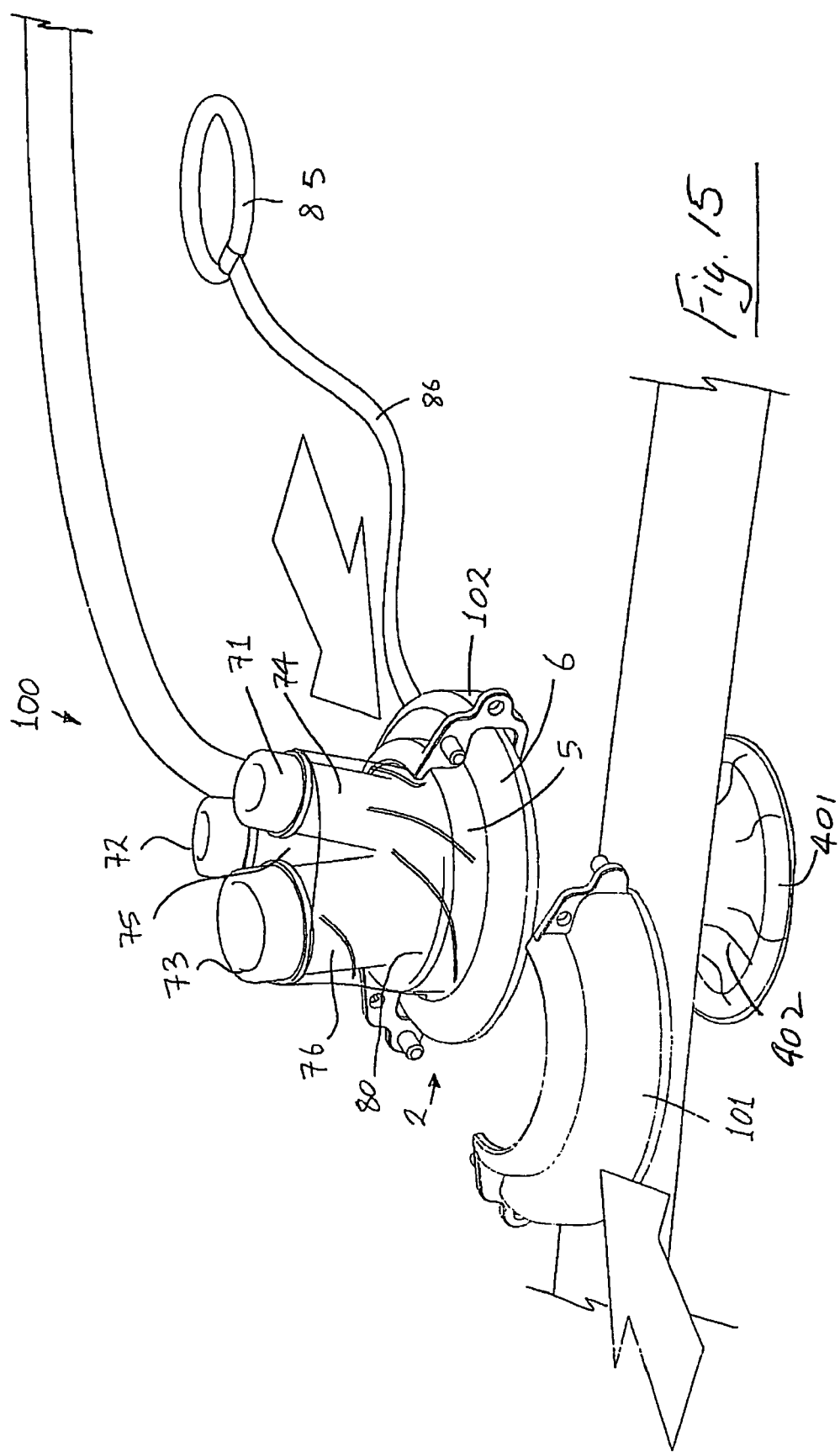
FIGS. 15 and 16 are isometric views of another instrument access device according to the invention, in use.
Figure 16:
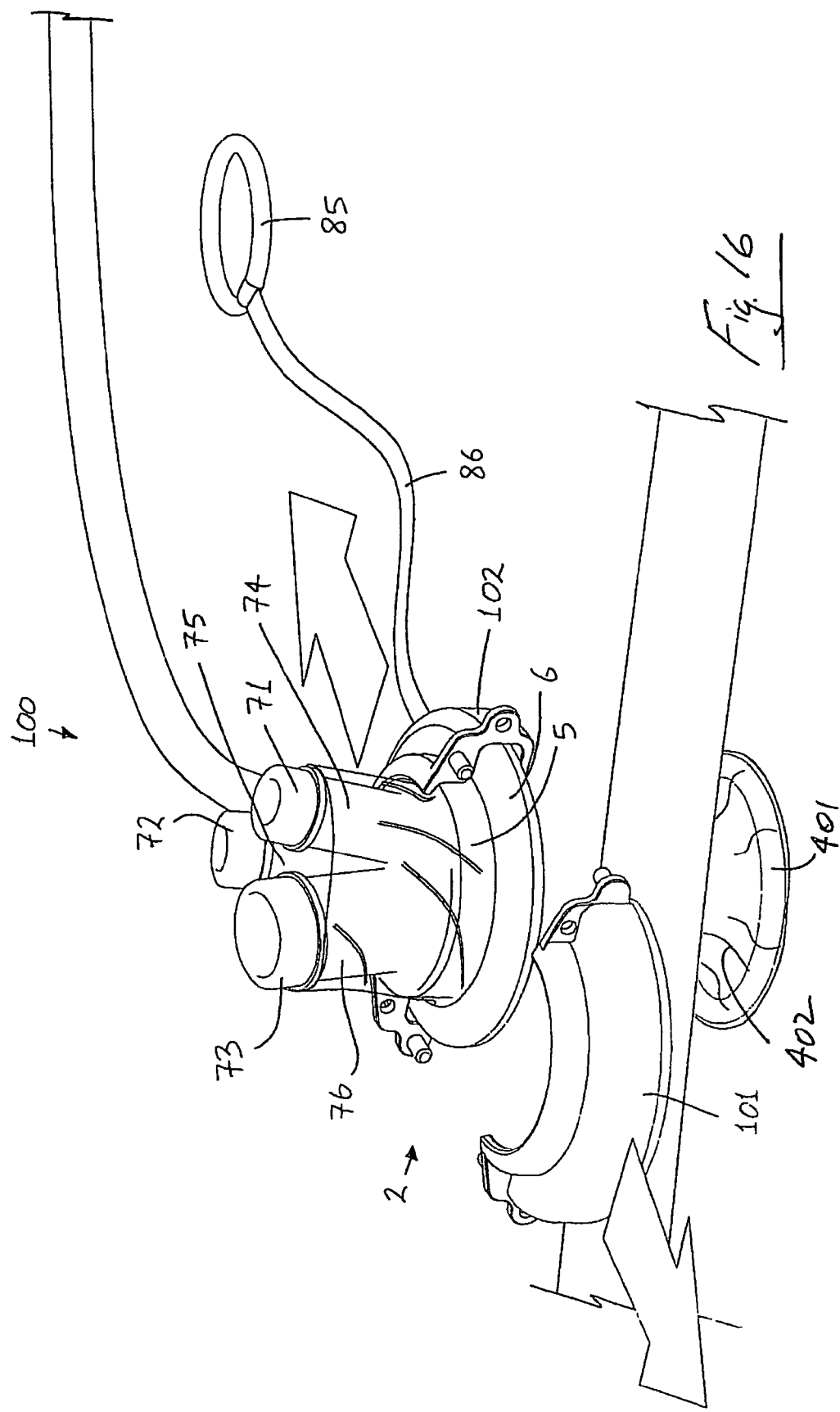

Referring to FIGS. 15 and 16 there is illustrated another instrument access device 100 according to the invention, which is similar to the instrument access device 70 of FIGS. 6 to 10, and similar elements in FIGS. 15 and 16 are assigned the same reference numerals.

In this case the device 100 comprises two clamp parts 101, 102. The clamp parts 101, 102 may be secured together around the connector base 80 and the proximal ring assembly 2 to clamp the connector base 80 to the proximal ring assembly 2.

Figure 17:
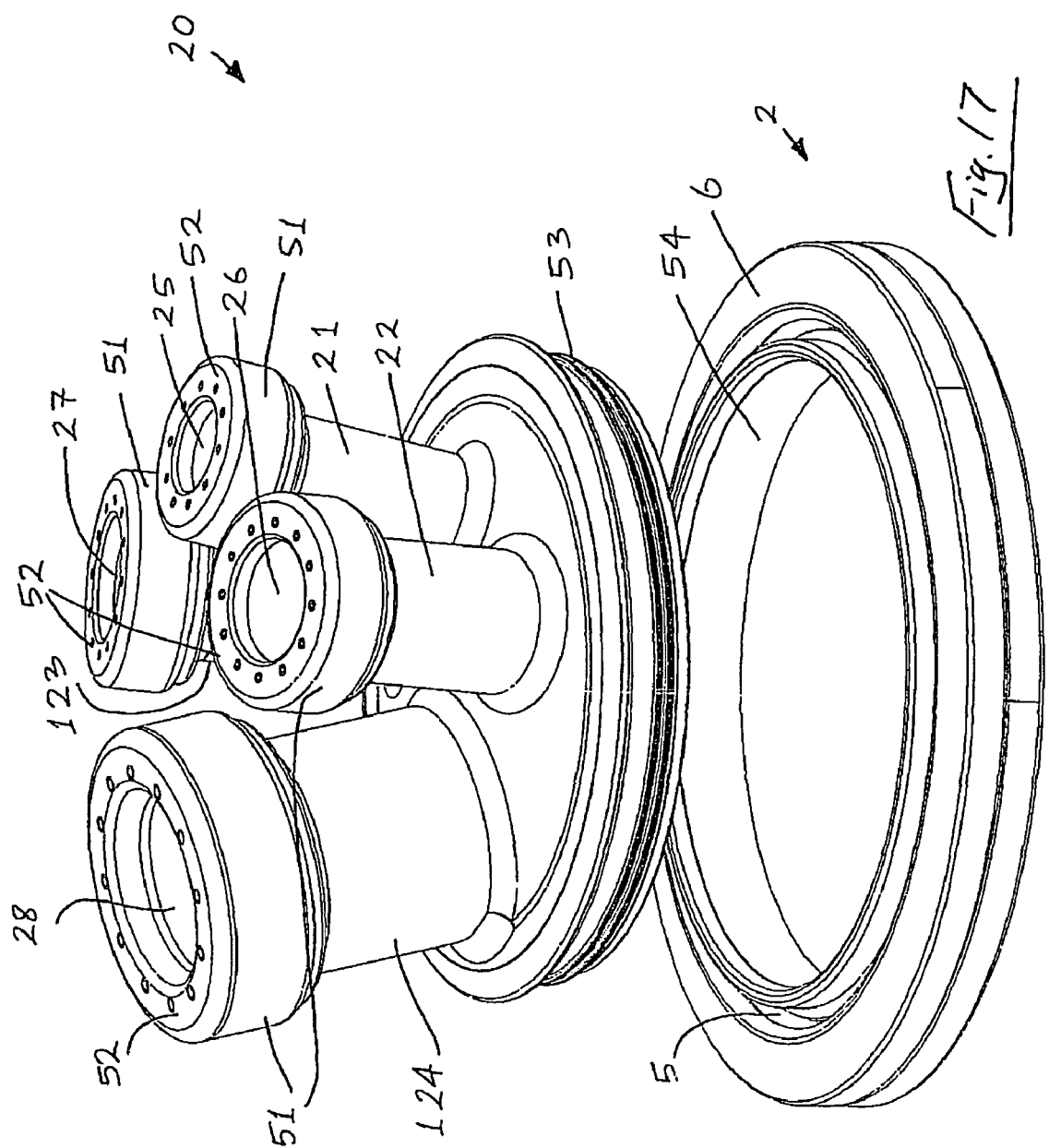
FIG. 17 is an exploded, isometric view of another instrument access device according to the invention.
Figure 18:
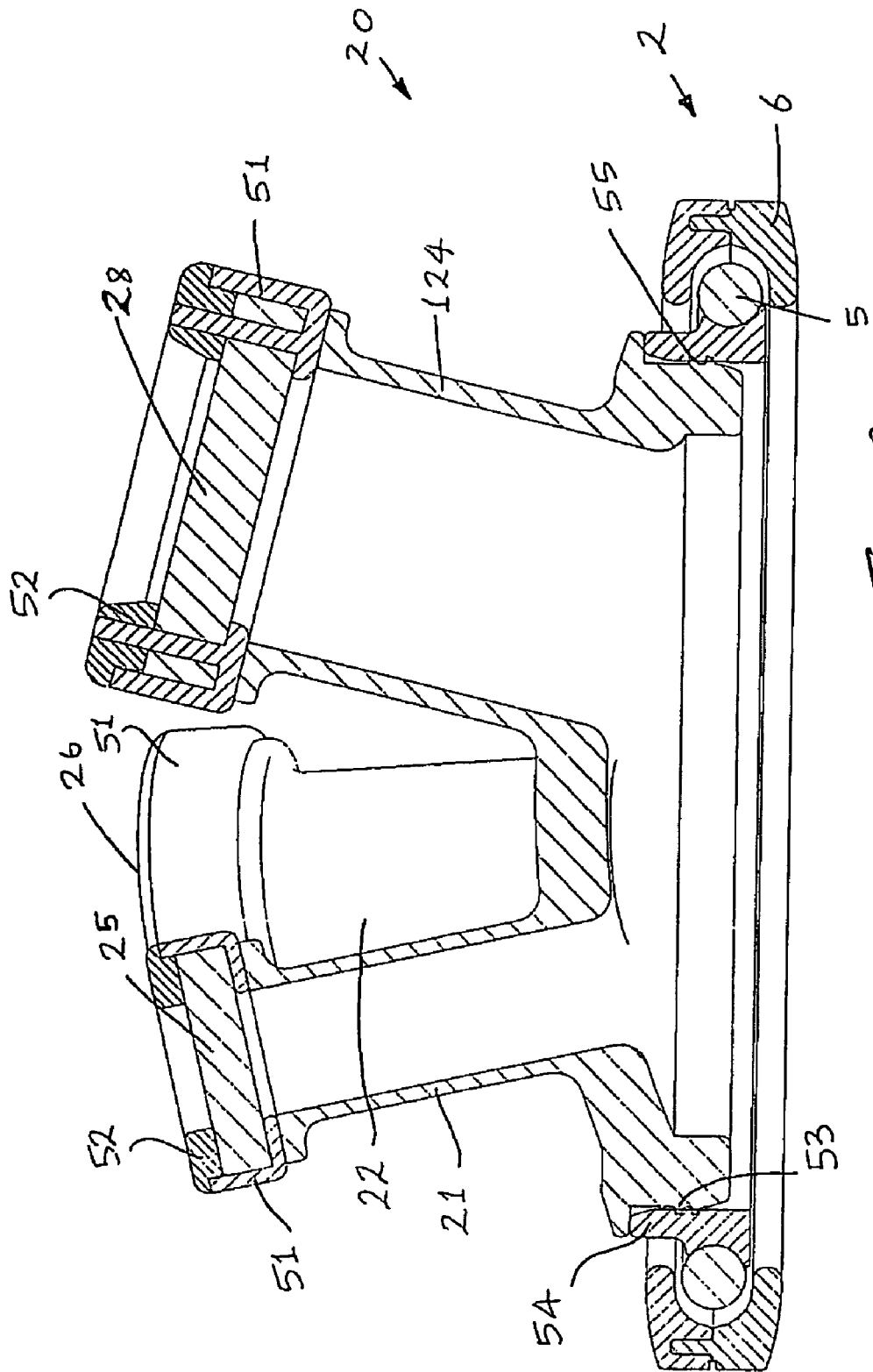
FIG. 18 is a view similar to FIG. 3 of the instrument access device of FIG. 17.

FIGS. 17 and 18 illustrate a further instrument access device 20 according to the invention, which is similar to the instrument access device 10 of FIGS. 4 and 5, and similar elements in FIGS. 17 and 18 are assigned the same reference numerals.

In this case the device 20 comprises a first instrument seal 25, a second instrument seal 26, a third instrument seal 27, a fourth instrument seal 28, a first connector sleeve 21, a second connector sleeve 22, a third connector sleeve 123, and a fourth connector sleeve 124.

Each instrument seal 25, 26, 27, 28 may be employed to effect a seal around a separate instrument extended through the device 20. Each instrument seal 25, 26, 27, 28 is formed separately from the other instrument seals 25, 26, 27, 28, and is spaced apart from the other instrument seals 25, 26, 27, 28. The first instrument seal 25 has a smaller diameter than the second instrument seal 26. The second instrument seal 26 has a diameter equal to the diameter of the third instrument seal 27. The fourth instrument seal 28 has a larger diameter than the third instrument seal 27.

Each connector sleeve 21, 22, 123, 124 connects the proximal ring assembly 2 to one of the instrument seals 25, 26, 27, 28.

FIG. 17 illustrates the rubber multiport cap 20 with for example 5 mm port 25, 10 mm port 26, 10 mm port 27, 12 mm port 28, and integrally moulded sealing flanges 53. Various combinations of ports are possible. FIG. 17 also illustrates the proximal 'O' ring 5, the outer proximal ring 6, and a docking ring 54 for the rubber multiport cap. The device 20 is suitable for large incisions, for example 2-4 cm.

FIG. 18 illustrates the gel 25, for example 5 mm instrument port, the gel 26, for example 10 mm instrument port, the gel 28, for example 12 mm instrument port, the gel caps 52, the gel housings 55, the docking ring 54 for the rubber port cap, the gas seal engagement point 55, the proximal 'O' ring 5, and the outer proximal ring 6.

FIGS. 17 and 18 illustrate the series of valves 25, 26, 27, 28 mounted on the rubber offset tubes 21, 22, 123, 124. The offset sleeves 21, 22, 123, 124 are of rubber, which has enough lateral flexibility for full instrument range of motion, but the longitudinal structural rigidity of the rubber tubes 21, 22, 123, 124 means the surgeon can introduce an instrument as a single-handed procedure.

Referring to FIGS. 19 to 21 there is illustrated another instrument access device 30 according to the invention, which is similar to the instrument access device 10 of FIGS. 4 and 5, and similar elements in FIGS. 19 to 21 are assigned the same reference numerals.

In this case both the first connector sleeve 13 and the second connector sleeve 23 are of a longitudinally flexible material.

The first instrument seal 14 has a diameter equal to the second instrument seal 24.

The distal anchoring ring 31, the retractor member 32, the wound opening 33, the first instrument 34 extended through the device 30, and the second instrument 35 extended through the device 30 are illustrated in FIGS. 19 to 21.

FIGS. 19 to 21 illustrate the twin valve sleeves 13, 23. FIG. 19 illustrates the gel valve 24, the gel valve 14, and the "trousers" double sleeve 13, 23. FIG. 20 illustrates the instrument 34 inserted in the valve 14. FIG. 21 illustrates the instruments 34, 35 in both the gel valves 14, 24. Each can be manipulated easily without causing leakage in the other.

The port 30 has at least two separate valves 14, 24 for individual instruments 34, 35. Each valve 14, 24 have its own sleeve portion 13, 23. Consequently, movement of any instrument 34, 35 should not affect the seal around any other instrument 34, 35.

In FIGS. 22 to 25 there is illustrated another instrument access device 40 according to the invention, which is similar to the instrument access device 30 of FIGS. 19 to 21, and similar elements in FIGS. 22 to 25 are assigned the same reference numerals.

In this case the instrument seals 14, 24 are located at the proximal ring assembly 2. No connector sleeves are provided.

FIG. 22 illustrates the first gel 14, a dividing wall 56, and the second gel 24. FIG. 23 is a plan view of the device 40. FIG. 24 illustrates the first gel semicircle 14, the second gel semicircle 24, and holes 57 for locating pins. The gels 14, 24 are split in two. Two instruments 34, 35 can be used. Because they are in independent gels 14, 24 neither causes leaks in the other.

Referring to FIGS. 26 to 48 there is illustrated a method of performing a surgical procedure according to the invention. In this case the surgical procedure performed is a laparoscopic cholecystectomy procedure.

A number of medical devices may be employed to perform the procedure for example a scalpel 201, an introducer device 202, an instrument access device 203, an insufflator 204, a camera device 205, and various surgical instruments 206.

Figure 27:
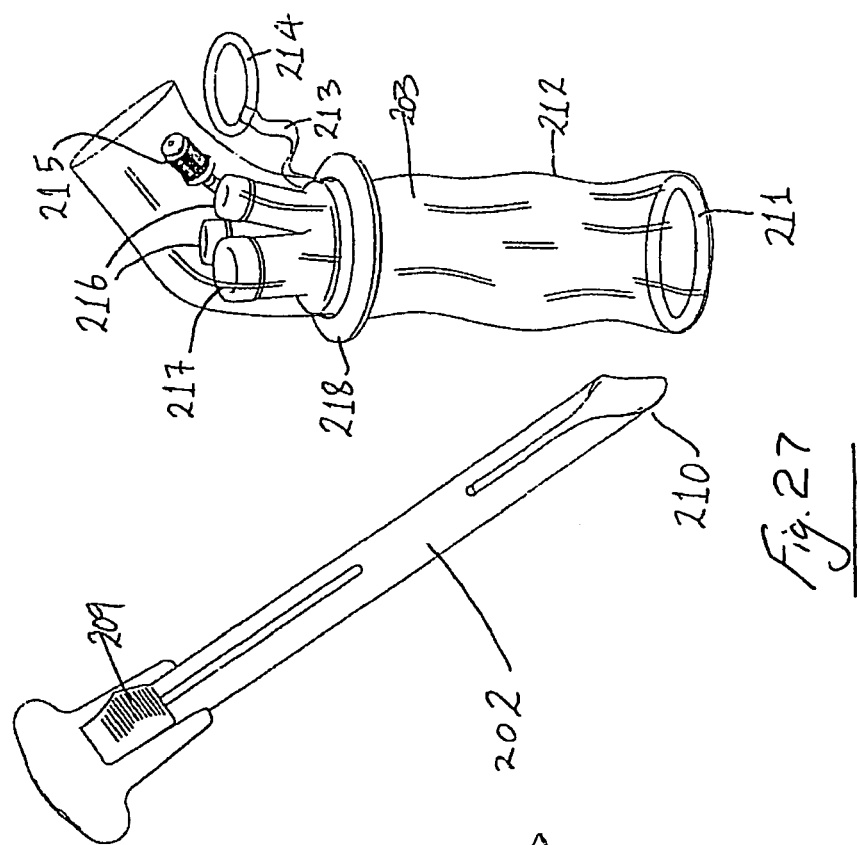
FIG. 27 is an isometric view of medical devices suitable for use in performing a surgical procedure according to the invention.

In use, the introducer device 202 and the instrument access device 203 are supplied in a pack 207. The pack 207 is opened (FIG. 26), and the introducer device 202 and the instrument access device 203 are removed from the pack 207 (FIG. 27).

Figure 26:
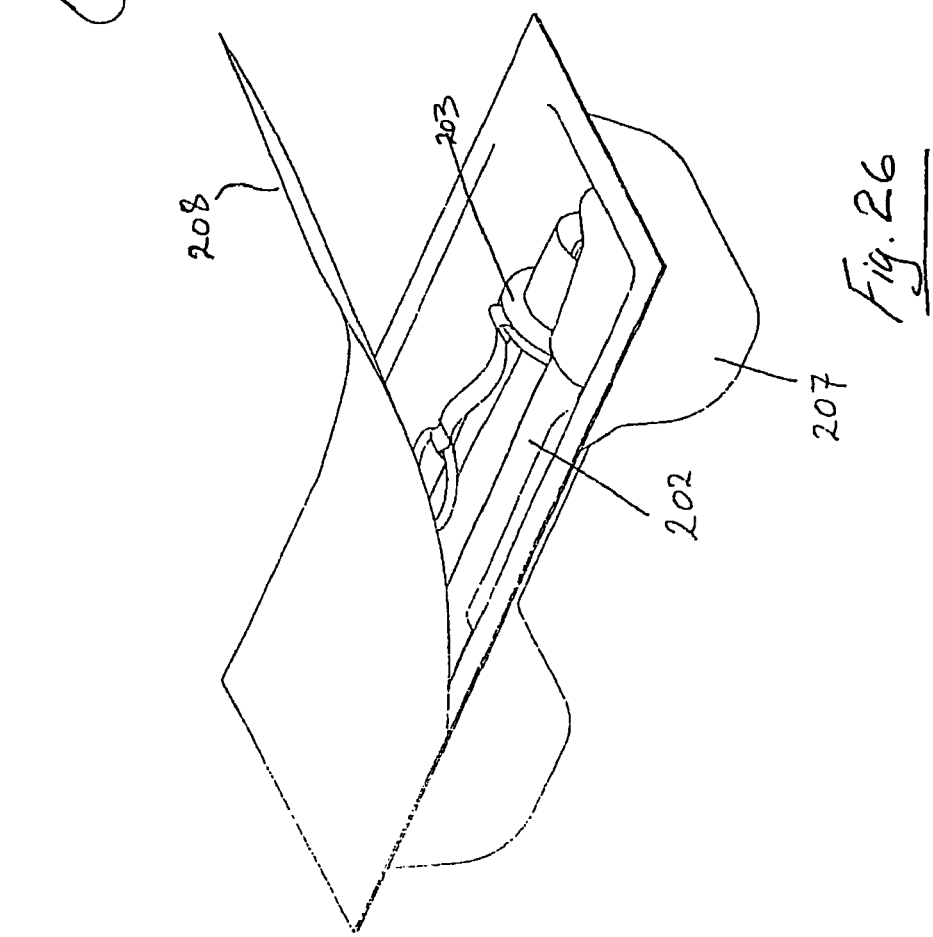
FIG. 26 is an isometric view of a pack.

FIG. 26 illustrates the peel off lid 208, the triport device 203, the injector introducer 202, and the plastic blister pack tray 207 which is a sterile pack. In FIG. 26 the user peels open the tray lid 208. FIG. 27 illustrates the injector introducer 202, the thumbswitch 209, the blunt dissecting tip 210, the distal ring 211, the sleeve 212, the removal ribbon 213, the removal ring 214, the insufflation line 215, the 5 mm ports 216, the 12 mm port 217, and the outer proximal ring 218. In FIG. 27 the user removes the introducer 202, and the triport 203.

Figure 29:
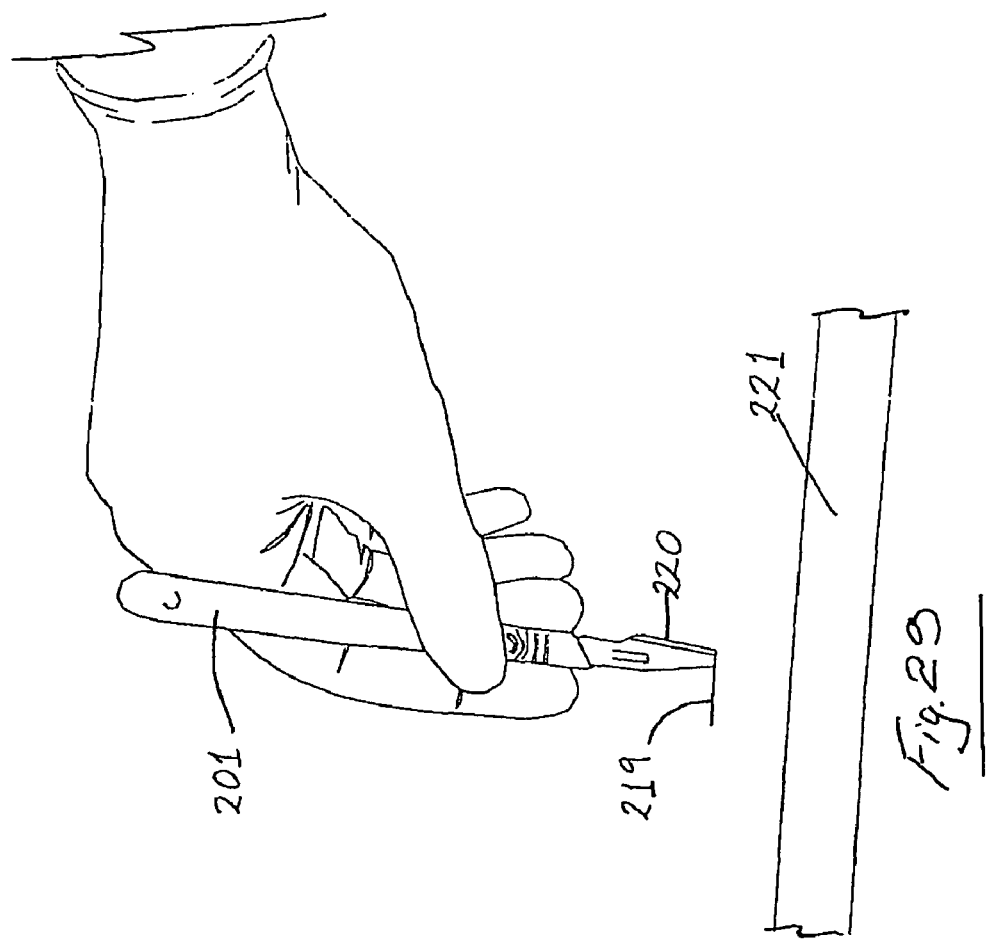
FIGS. 28 to 36 are isometric views illustrating insertion of an instrument access device into a wound opening.

The distal ring 211 of the instrument access device 203 is inserted into the introducer device 202 (FIG. 28), and the scalpel 201 is used to create a wound opening 219 (FIG. 29).

Figure 28:
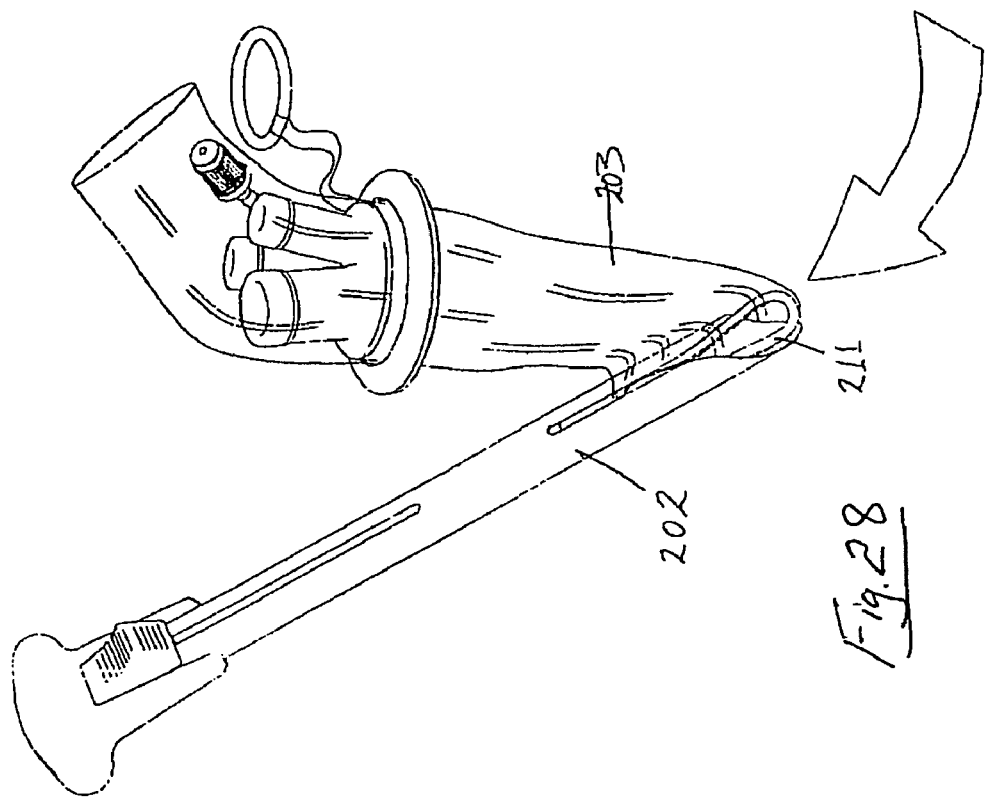

In FIG. 28 the user inserts the distal ring 211 into the end of the injector introducer 202. FIG. 29 illustrates the scalpel 201, the blade 220, and the abdominal wall 221. In FIG. 29 the surgeon creates either a 15-20 mm skin incision 219 through the skin and the fascia layers but not through the peritoneum, or cuts all the way through to the abdominal cavity with a Hasson cut-down incision 219.

Figure 31:
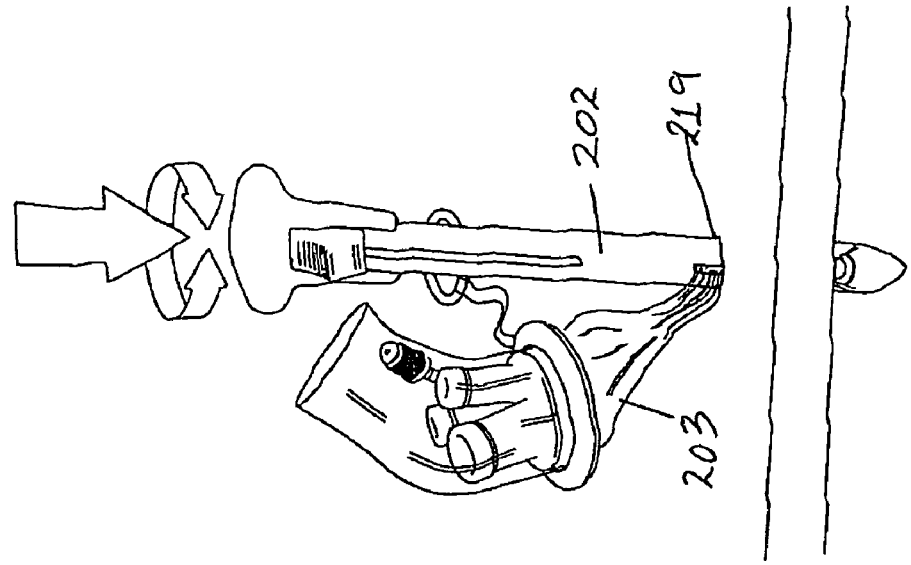
Figure 30:
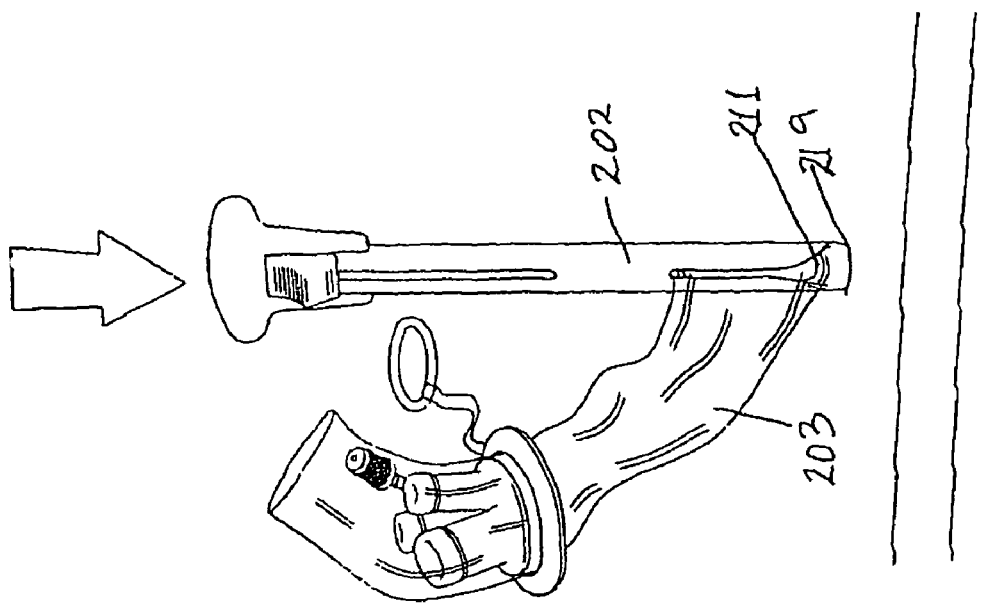

The introducer device 202 is inserted through the wound opening 219 until the distal ring 211 of the instrument access device 203 is within the wound interior (FIGS. 30 and 31).

In FIG. 30 the tip of the injector introducer 202 is placed in the skin incision 219 or the Hasson cut-down incision 219. In the case of the skin incision, downward pressure and axial rotation of the injector introducer 202 cause the blunt dissecting tip 210 to burrow through the peritoneum to the abdomen (FIG. 31). This may take place while the abdomen is insufflated. In the case of the Hasson cut-down incision, the injector 202 is easily passed through the pre-made incision (FIG. 31).

Figure 33:
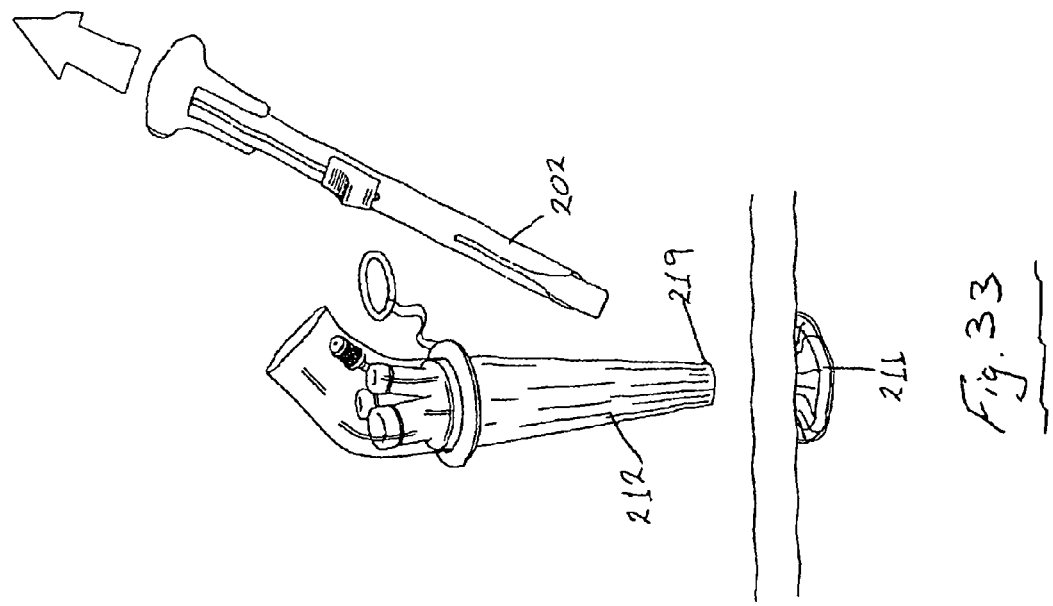

The thumbswitch 209 of the introducer device 202 is depressed to eject the distal ring 211 of the instrument access device 203 into the wound interior (FIG. 32), and the introducer device 202 is removed from the wound opening 219 (FIG. 33).

Figure 32:
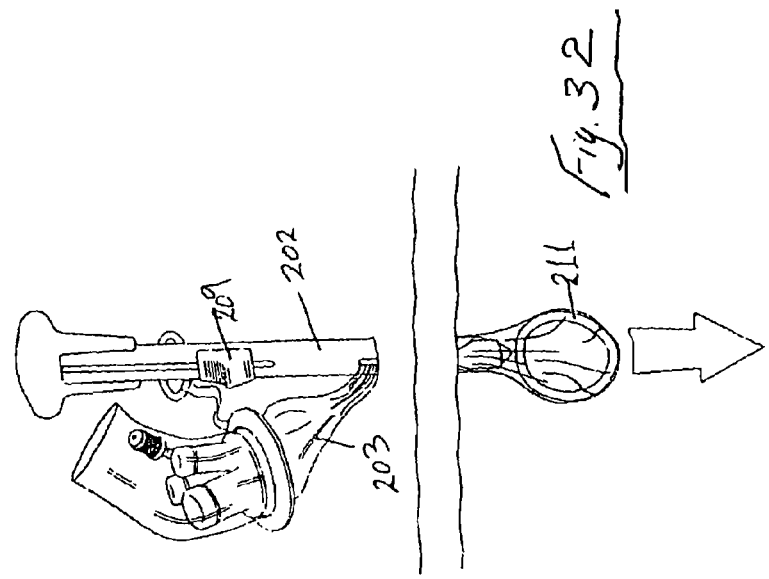

In FIG. 32 the thumbswitch 209 is pressed downwards to eject the distal ring 211. In FIG. 33 the injector introducer 202 is removed from the incision 219 leaving the distal ring 211 in the abdomen. The sleeve 212 is pulled upwards to engage the distal ring 211 with the underside of the abdominal wall.

Figure 34:
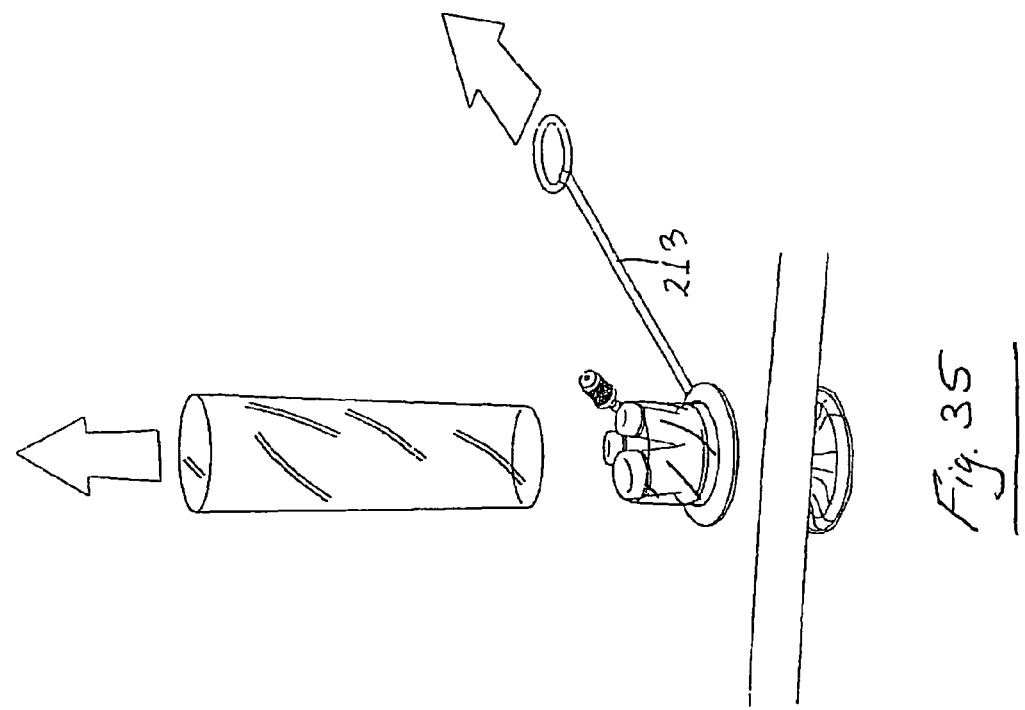
Figure 35:
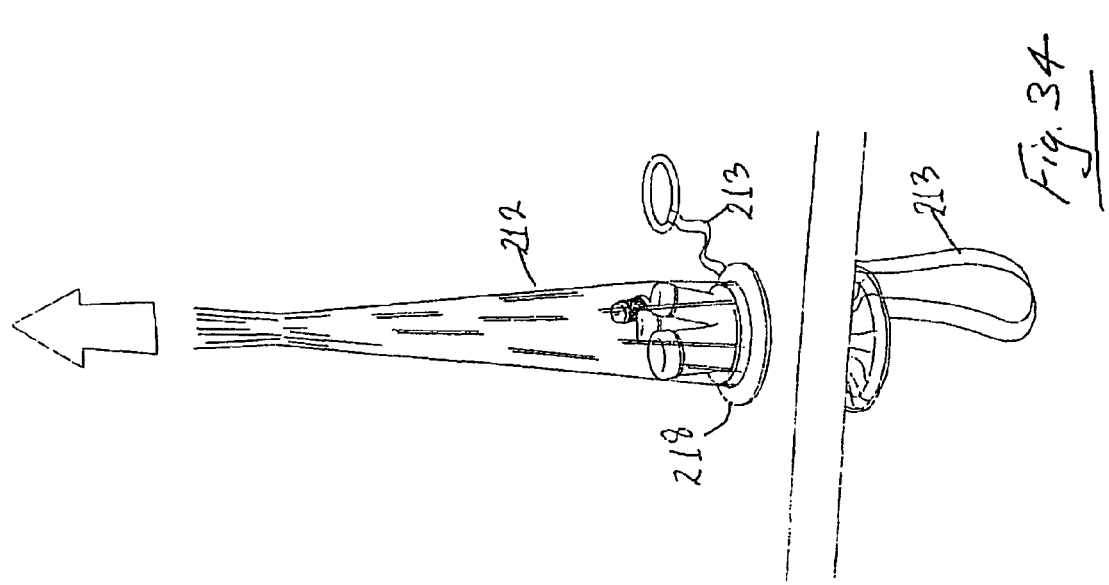

The sleeve 212 of the instrument access device 203 is pulled proximally and the outer proximal ring 218 is pushed distally to retract laterally the sides of the wound opening 219 (FIG. 34). The excess sleeve material is cut-away, and the removal ribbon 213 is pulled proximally to remove any excess ribbon from the wound interior (FIG. 35).

In FIG. 34, the user keeps upward tension on the sleeve 212, and the outer proximal ring 218 is pushed down until sufficient retraction is achieved. In FIG. 35 the removal ribbon 213 is gently pulled to remove slackness from inside the abdomen. The excess sleeve 212 is cut and removed.

Figure 37:
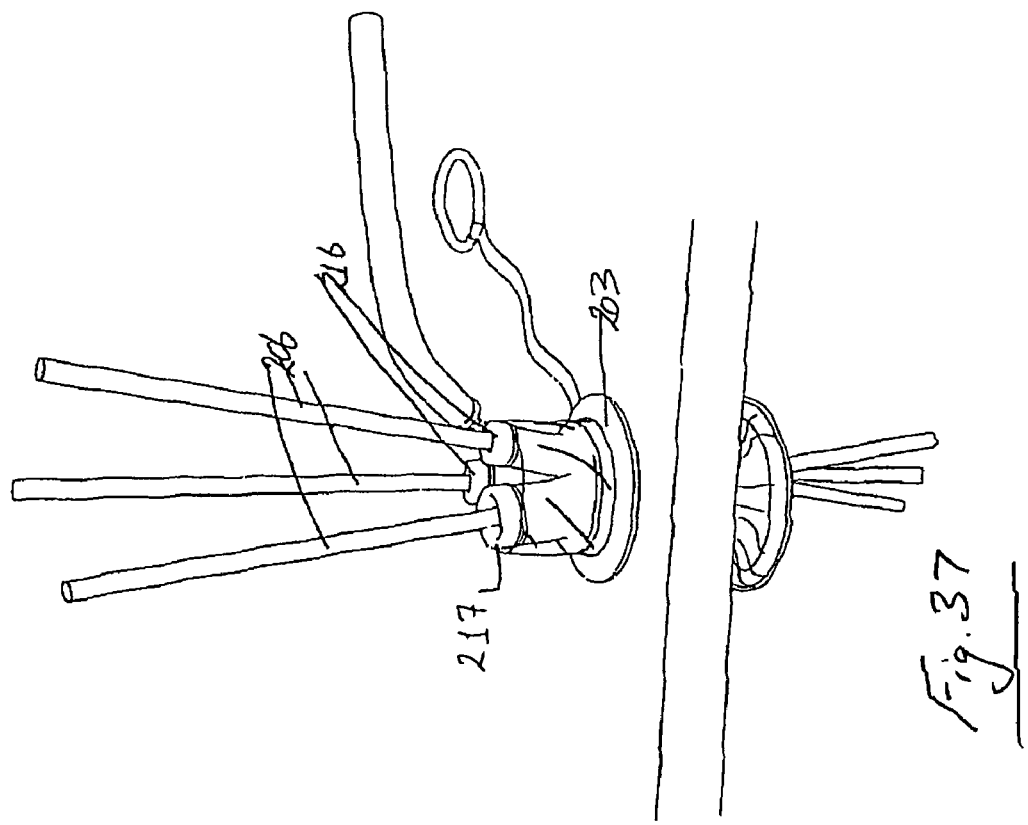
FIGS. 37 to 44 are isometric views illustrating performing a surgical procedure using surgical instruments inserted through the instrument access device of FIGS. 28 to 36.

The insufflator 204 is connected to the insufflation line 215 to insufflate the abdomen (FIG. 36), and one or more instruments 206 may be inserted through the ports 216, 217 (FIG. 37).

Figure 36:
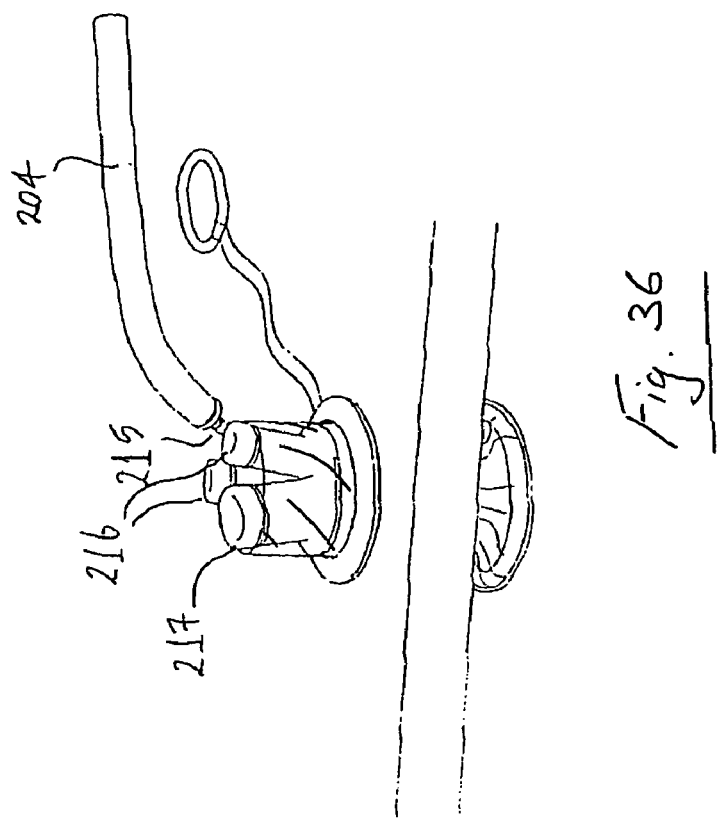

FIG. 36 illustrates the insufflation supply 204, the insufflation line 215, the gel ports 216, 217. In FIG. 36 the insufflation line 215 is attached to the insufflation supply 204. In FIG. 37 up to three instruments 206 may be used simultaneously through the triport 203. Each leg 216, 217 have an individual gel valve on top. The legs 216, 217 are rubbery and so can accommodate the instruments 206 moving off axis. Moving one instrument 206 does not cause leaks in either of the other two instruments 206.

Figure 38:
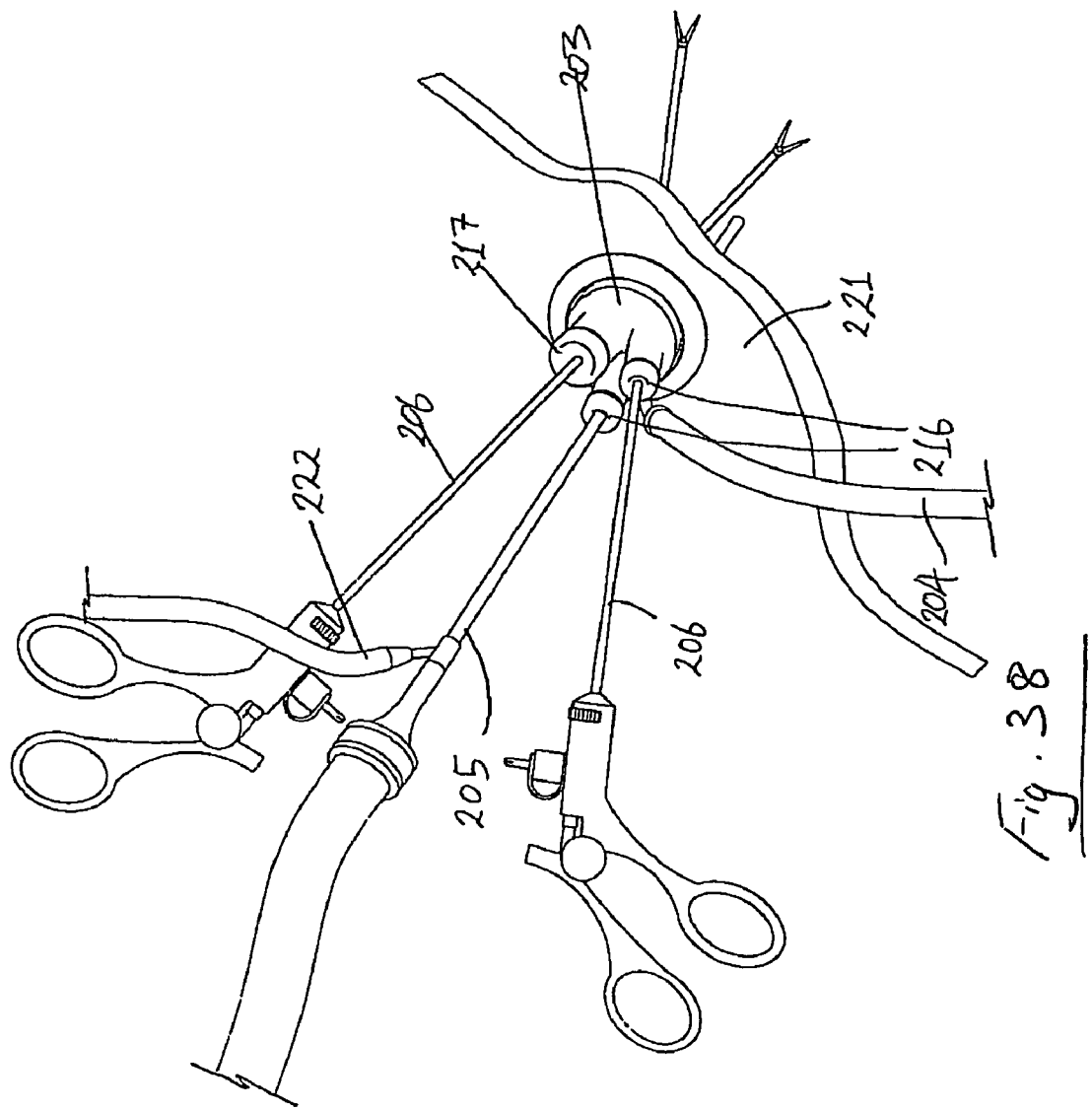

Instruments 206 may be inserted through the ports 216, 217 of the instrument access device 203 to access the wound interior, and/or the camera 205 may be inserted through one of the ports 216, 217 to access the wound interior (FIG. 38). In this case the camera 205 has a light source 222 inclined at an angle to the longitudinal axis of the camera 205, and the instruments 206 are straight.

In FIG. 38 there are two 5 mm ports 216 and one 12 mm port 217. FIG. 38 illustrates the 5 mm camera 205, the 5 mm instruments 206, the insufflation supply 204, the abdominal wall 221, and the 12 mm port 217.

Figure 39:
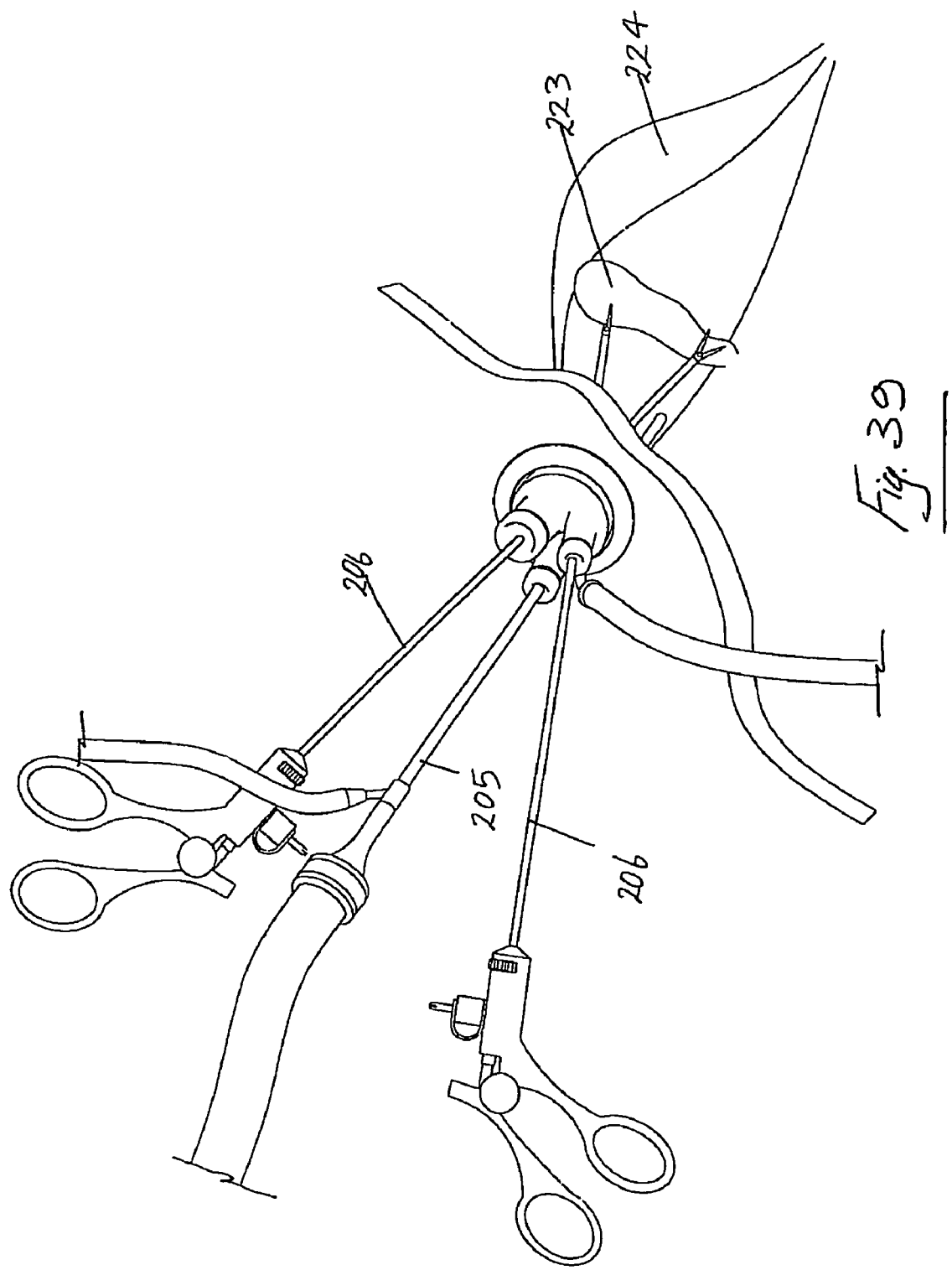

One of the instruments 206 may be used to pivot the gall bladder 223 upwards and also pivot the liver 224 upwards (FIG. 39). The other instrument 206 may then be issued to clamp the cystic bile duct and to sever the gall bladder 223 for removal.

FIG. 39 illustrates the straight retracting instrument 206, the gall bladder 223, the liver 224, and the dissecting instrument 206. In FIG. 39 the straight retracting instrument 206 grasps the gall bladder 223 and lifts it up. This also retracts the liver 224 out of the way. The dissecting instrument 206 can then isolate the gall bladder 223. Vision is provided by the 5 mm scope 205.

Figure 40:
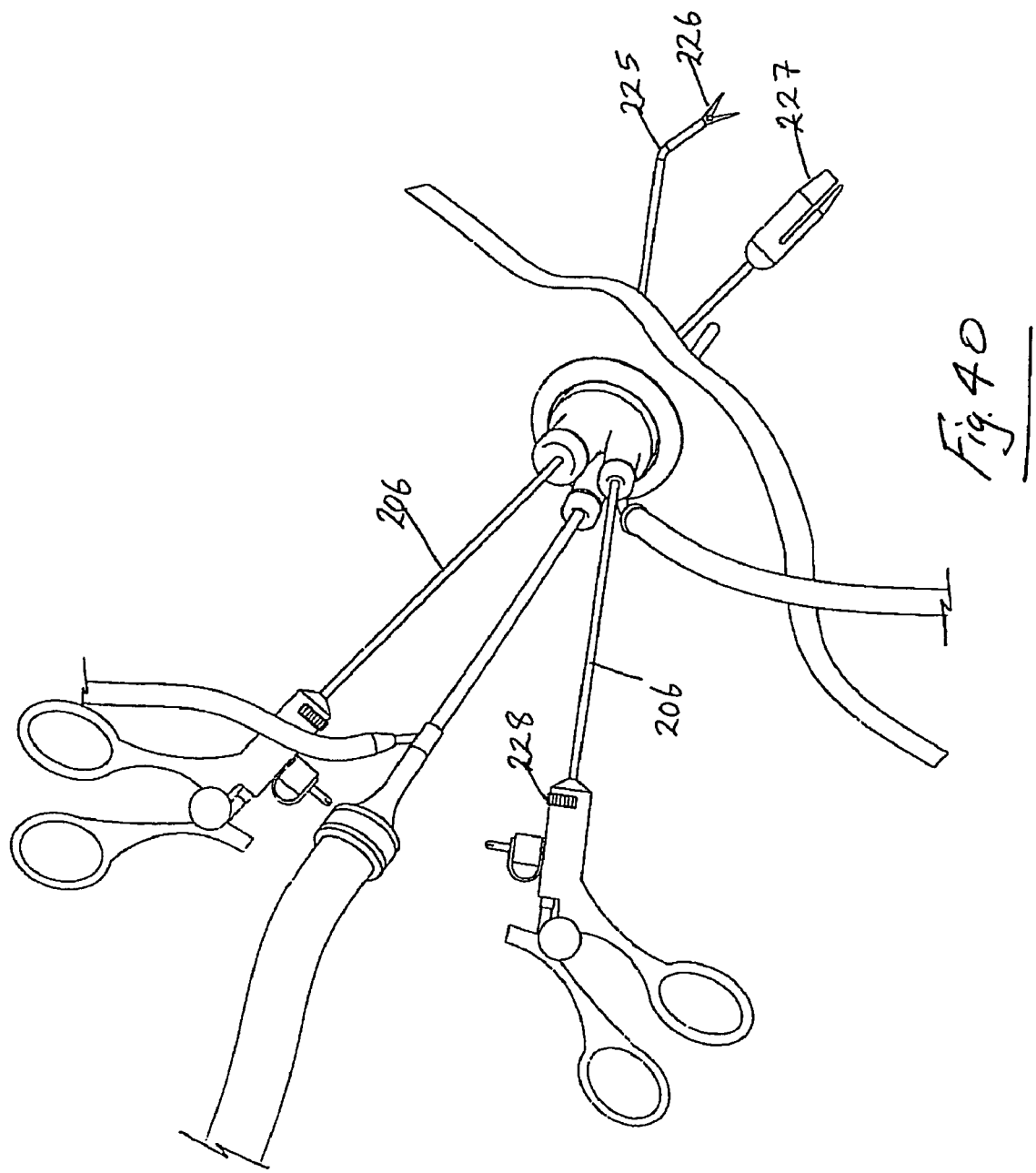
Figure 41:
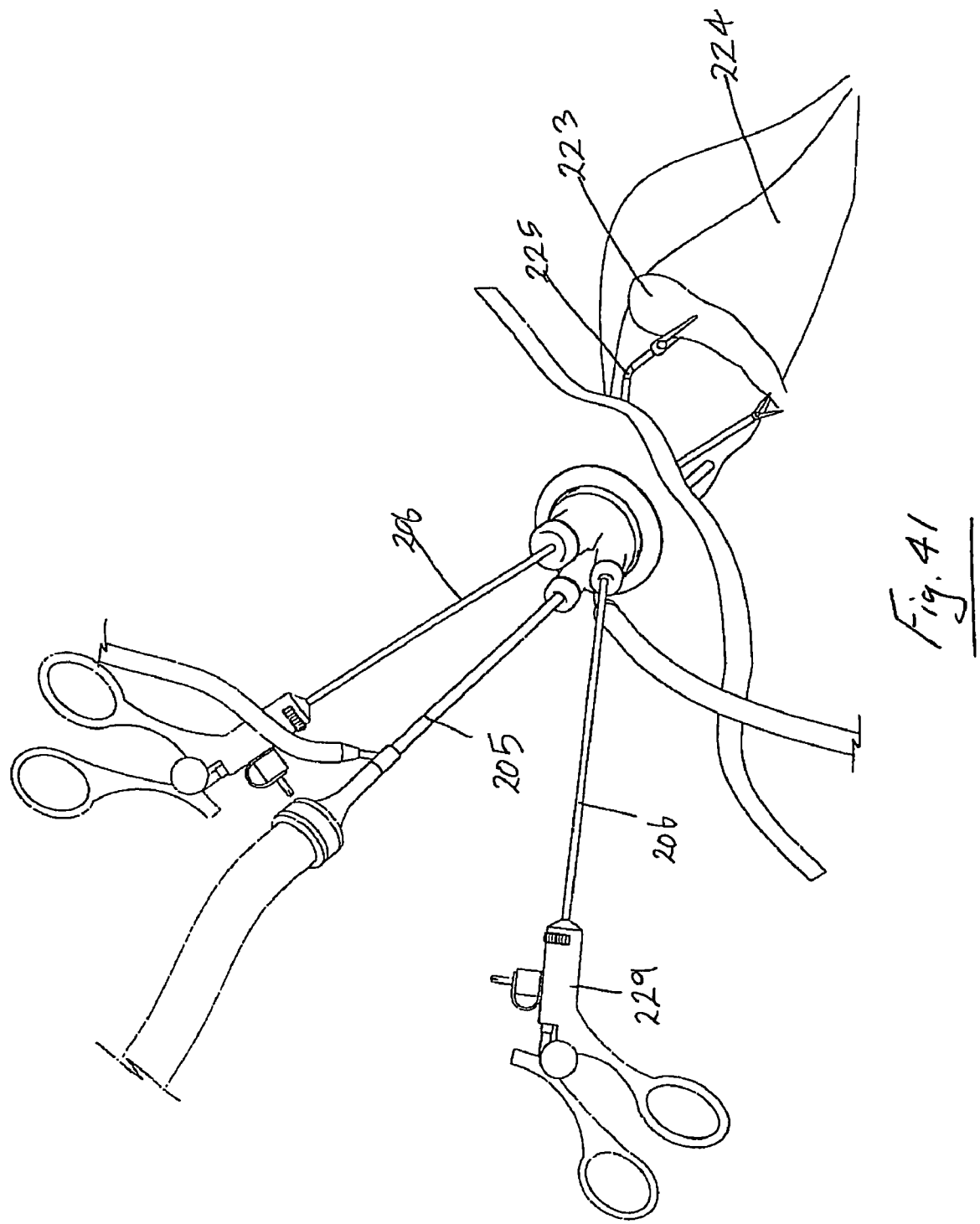

One of the instruments 206 may have a bend or curved section 225 close to the instrument distal end (FIGS. 40 and 41). The bend section 225 may be a fixed bend.

FIG. 40 illustrates the 5 mm shaft 206, the bent/bendable instrument 206 with the end effector 226 which may rotate, the 12 mm end effector 227, and the rotating thumbwheel 228 which may rotate the end effector 226.

FIG. 41 illustrates the bent instrument 206 retracting the gall bladder 223, the liver 224, and the increased distance between the instrument handle 229 and the laparoscope 205. Using the retracting instrument 206 with the bend 225 near the end effector 226 or near the handle 229 or both, enables the handle 229 to rest further away from the laparoscope 205 and other instrument handles, thereby reducing clutter/interference.

Figure 42:
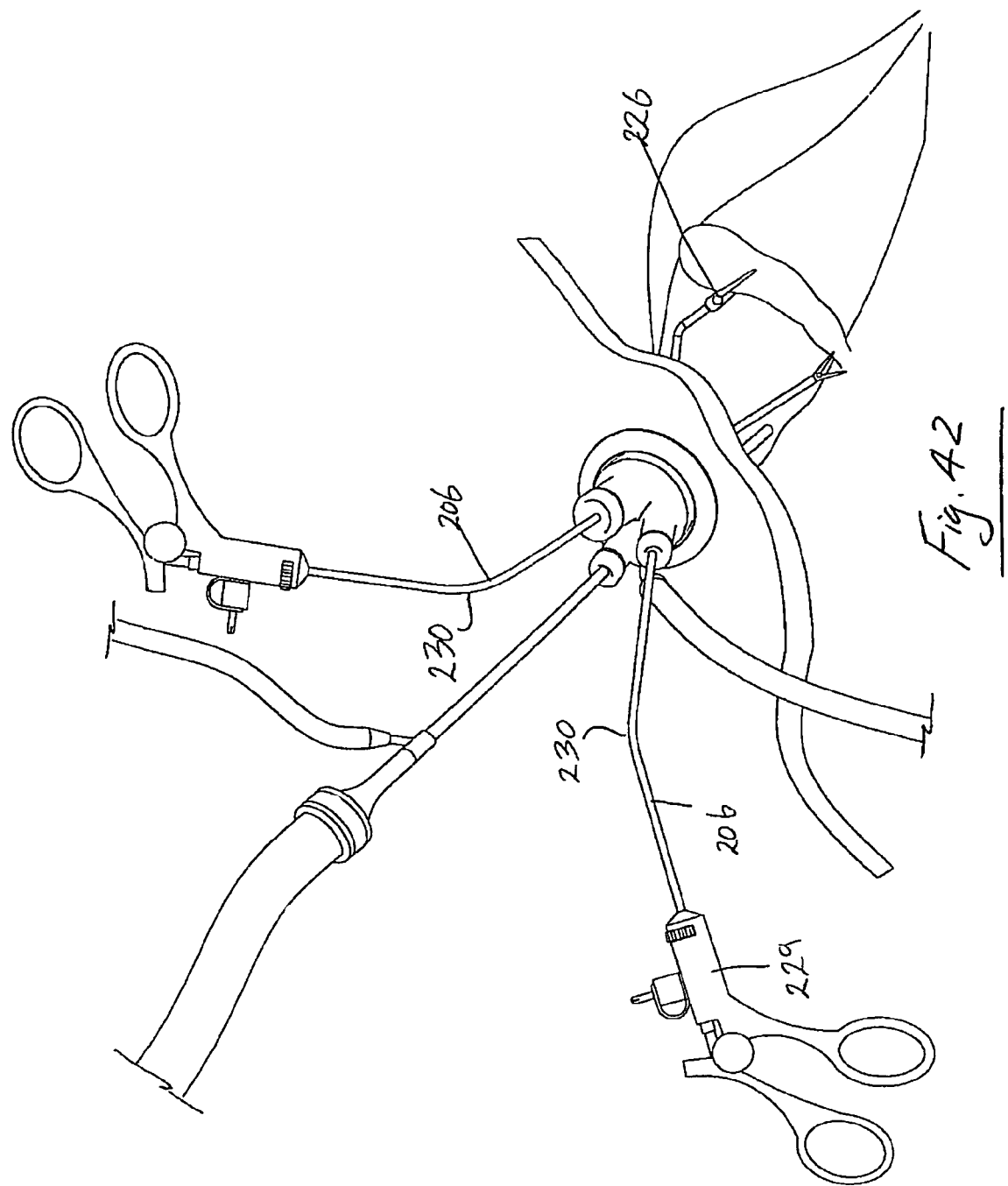

One or more of the instruments 206 may have a bend or curved section 230 close to the instrument proximal end (FIG. 42).

In FIG. 42 the bendable or bent shafts 206 near the handle 229 and/or the end effector 226 may increase the space available for the surgeon's hands.

The radius of curvature of the bend or curved section 225 of the instrument 206 and the length of the end effector 226 may be varied to suit requirements. For example, in FIGS. 43 and 44, the instrument 206 has a larger radius of curvature bent/curved section 225, and a larger end effector 226. The light source 222 may be provided parallel to and in-line with the longitudinal axis of the camera 205 (FIGS. 43 and 44).

Figure 43:
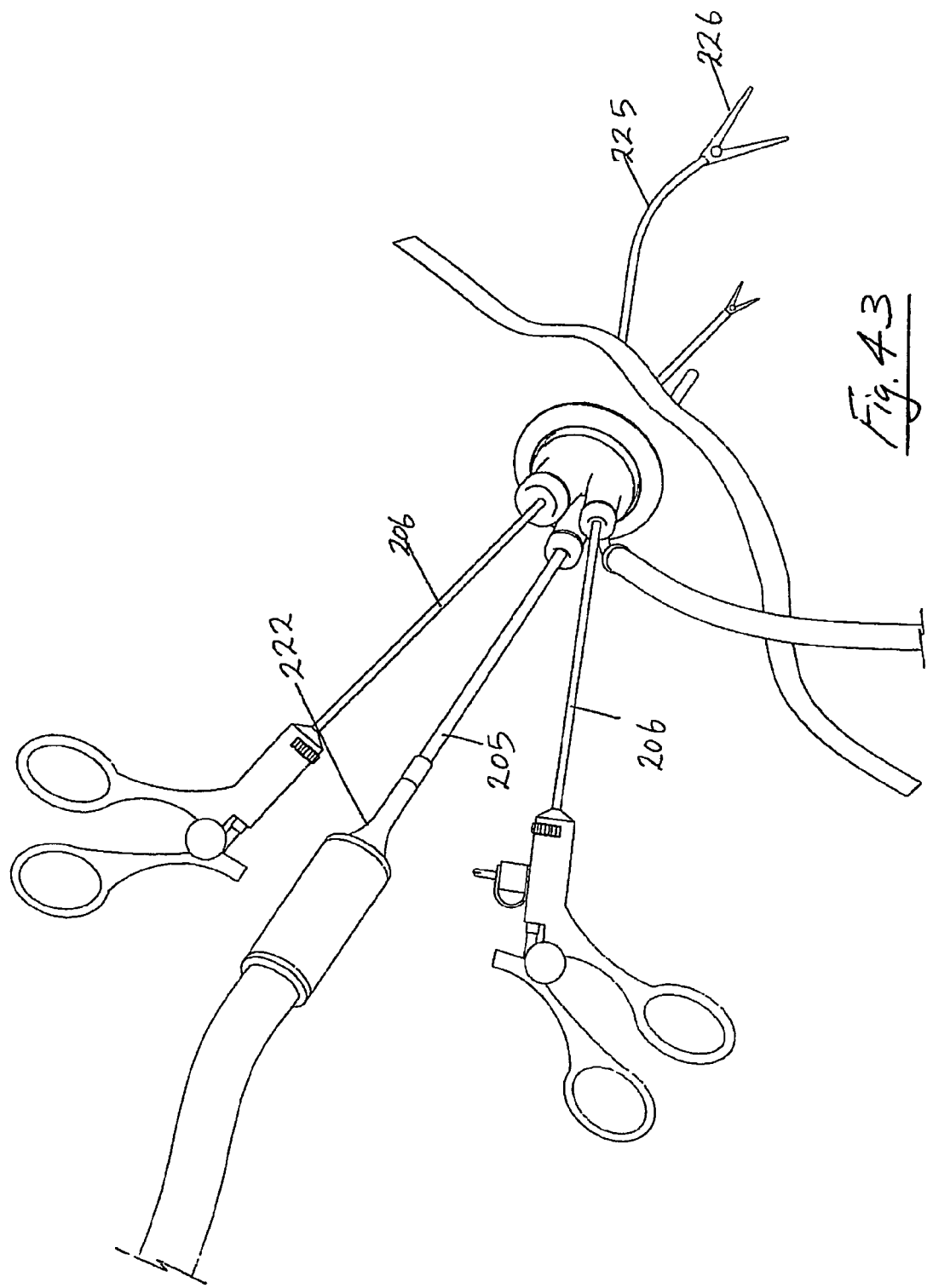

FIG. 43 illustrates the in-line light source 222 on the laparoscope 205, the curved shaft 206, and the large head grasper 226, e.g. up to 4 cm.

Figure 44:
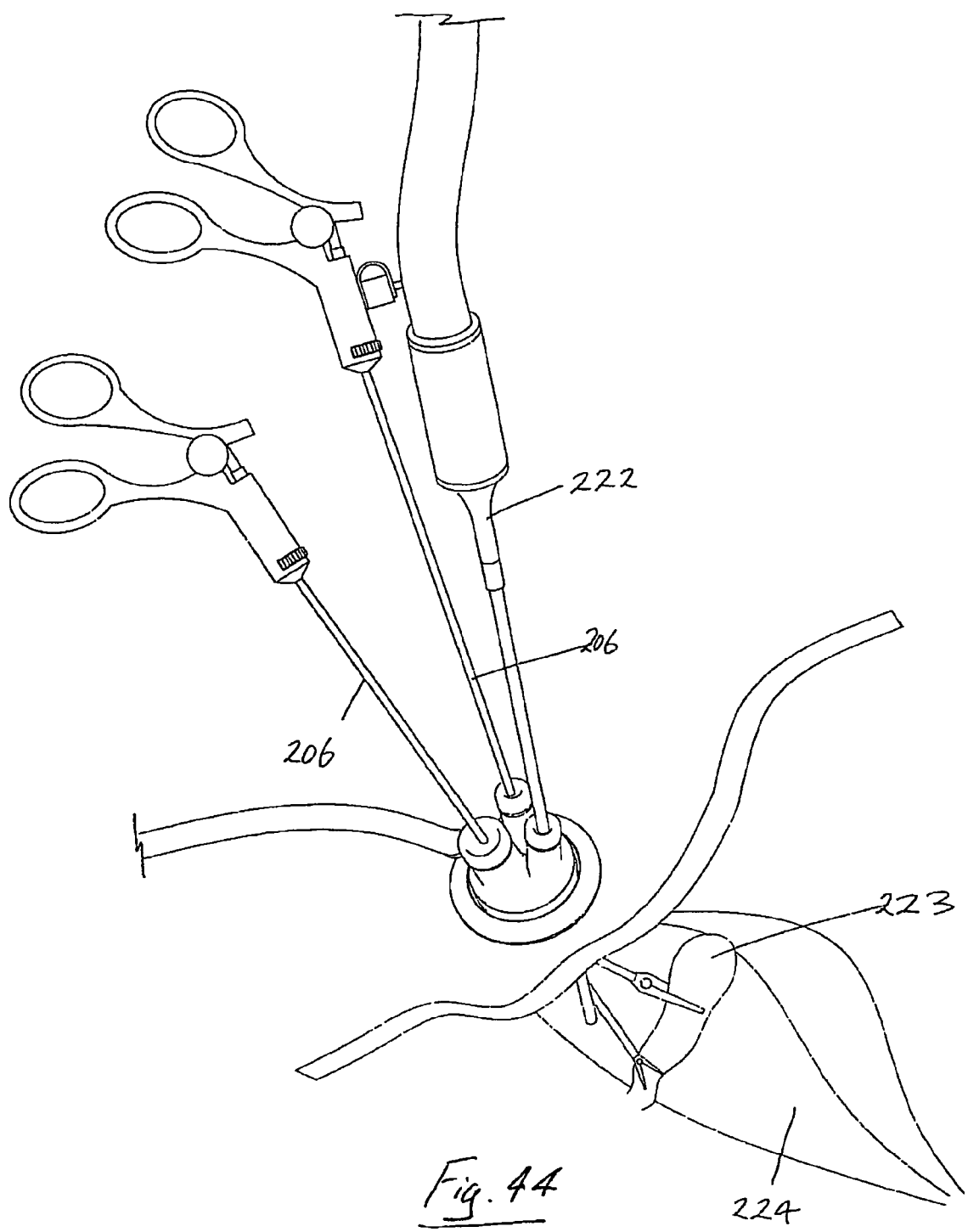

FIG. 44 illustrates the grasping instrument 206 in the non-dominant hand, the dissecting instrument 206 in the dominant hand, the in-line light source 222, the gall bladder 223, and the liver 224.

Figure 46:
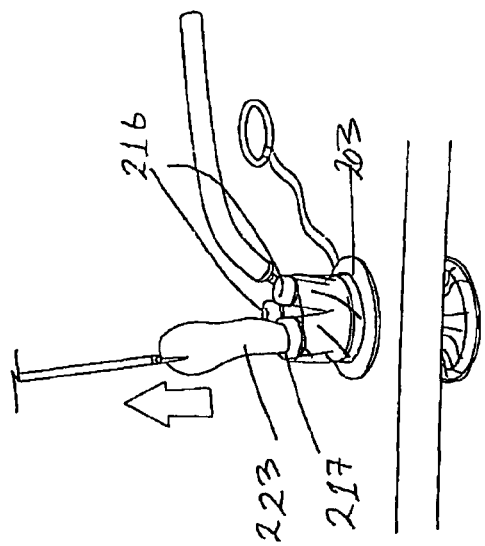
FIGS. 45 to 48 are isometric views illustrating removal of a body part through the instrument access device of FIGS. 28 to 36.
Figure 45:
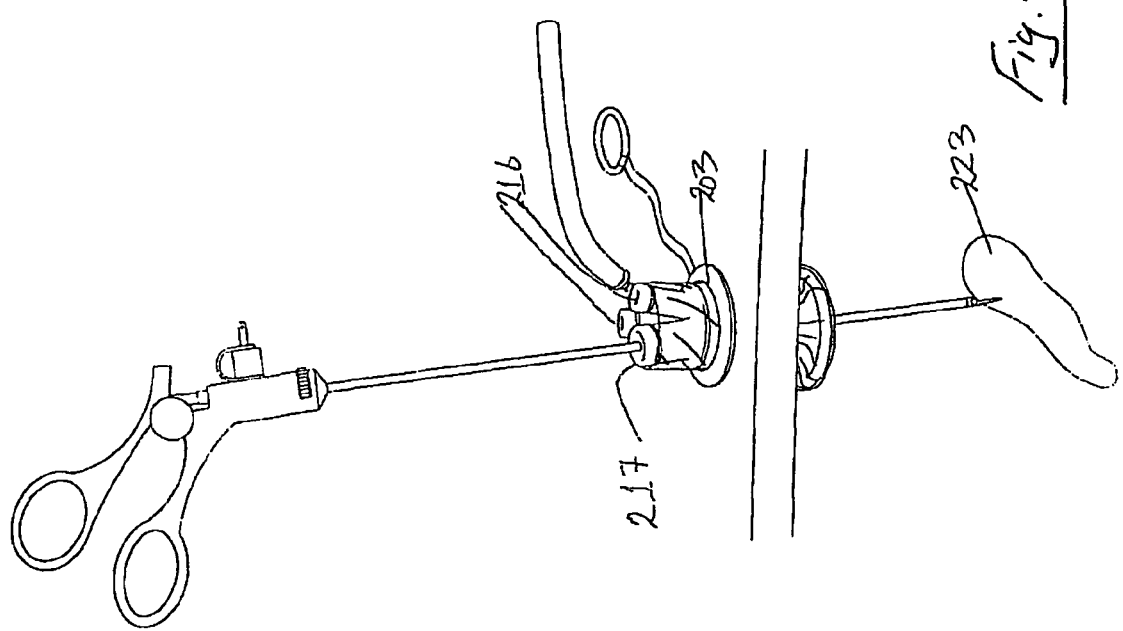
Figure 48:
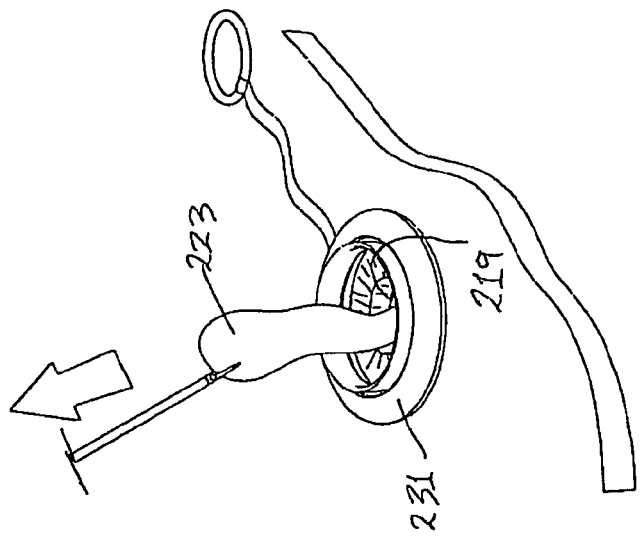

One or more body parts, for example the severed gall bladder 223 may be removed from the wound interior. The body part may be removed through the ports 216, 217 of the instrument access device 203 (FIGS. 45 and 46). Alternatively the valve ports 216, 217 may be detached from a retractor base 231 of the instrument access device 203 (FIG. 47), and the body part may be removed through the retractor base 231 (FIG. 48).

FIG. 45 illustrates the 12 mm valve 217, and the resected gall bladder 223. Due to the highly elastic nature of the gel material, specimens such as the gall bladder 223 may be extracted through the large 12 mm leg 217 of the triport 203 (FIG. 46).

Figure 47:
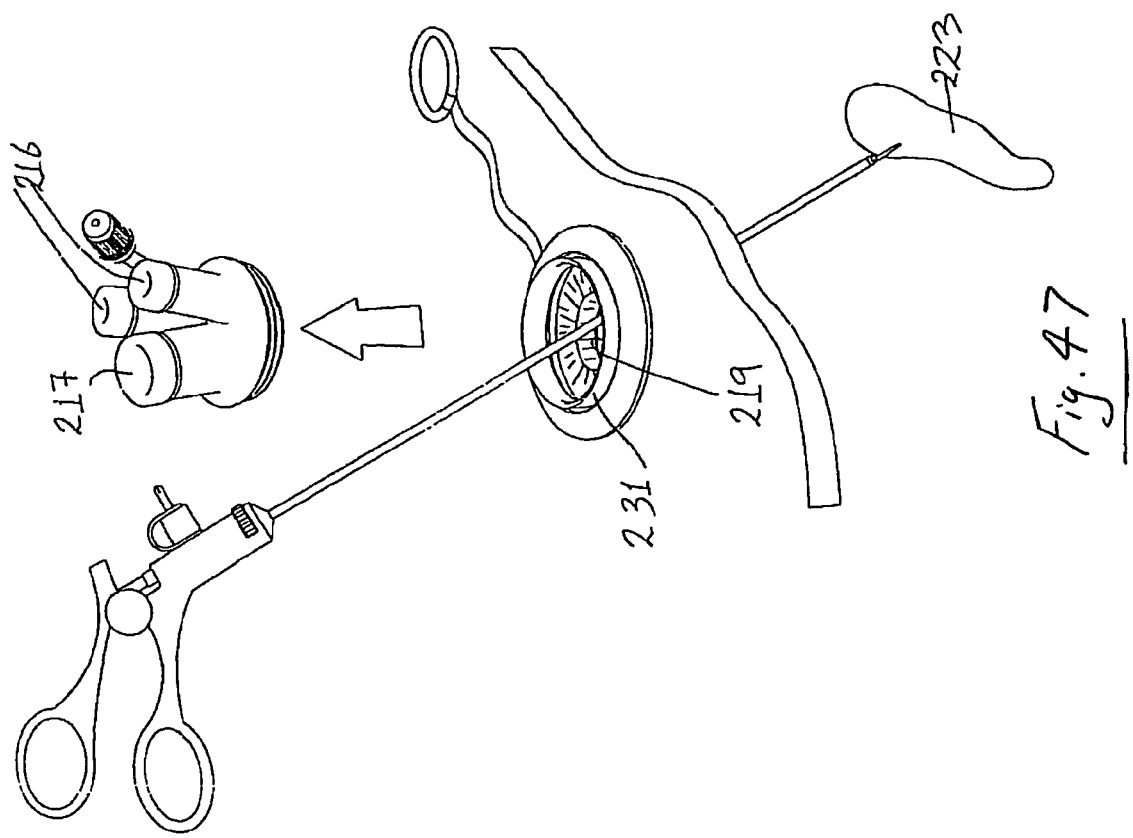

FIG. 47 illustrates the triport valves 216, 217 removed from the retractor base 231, the retracted and protected incision 219, and the resected gall bladder 223. The gall bladder 223 is easily removed through the retracted/protected incision 219 (FIG. 48). The triport valves 216, 217 may be re-attached for final laparoscopic examination prior to removing the device 203 at the end of the procedure.

Various features of the invention are described and illustrated. It will be appreciated that at least some of the features described in relation to one embodiment may be used not only in the embodiment specifically described but also in other appropriate embodiments.

The invention is not limited to the embodiments hereinbefore described, with reference to the accompanying drawings, which may be varied in construction and detail.

The invention claimed is:

1. An instrument access device comprising:
   a wound retractor including:
      a proximal ring-shaped portion for location externally of a wound opening;
      a distal ring-shaped portion for location within a wound interior;
      a retraction portion extending proximally from the distal portion to the proximal portion to retract laterally the sides of the wound opening; and
   a seal assembly including:
      a first instrument seal spaced proximally the proximal ring-shaped portion of the wound retractor and laterally movable with respect to the proximal ring-shaped portion;
      a second instrument seal spaced proximally the proximal ring-shaped portion of the wound retractor and laterally movable with respect to the proximal ring-shaped portion;
      a third instrument seal spaced proximally the proximal ring-shaped portion of the wound retractor and laterally movable with respect to the proximal ring-shaped portion; and
      the first instrument seal being larger than the second and third instrument seals; the second and third instrument seals having substantially the same size; and the first, second, and third instrument seals being oriented in a generally triangular at-rest configuration.

2. A device according to claim 1, wherein the seal assembly further includes separate, proximally extending connector tubes coupled to respective instrument seals.

3. A device according to claim 2, wherein each of the connector tubes is laterally flexible.

4. A device according to claim 2, wherein each of the connector tubes is oblique to one another and oblique to a longitudinal axis of the wound retractor.

5. A device according to claim 2, wherein each of the connector tubes is longitudinally rigid.

6. A device according to claim 1, further including a connector base portion configured to releasably mount the seal assembly to the proximal ring-shaped portion.

7. A device according to claim 6, wherein the connector base portion includes a proximally extending dome portion.

8. A device according to claim 6, wherein the connector base portion includes a radially outer protruding member configured to engage with a radially inner part of the proximal ring-shaped portion.

9. A device according to claim 1, wherein the seal assembly further includes an insufflation port separate from the instrument seals.

10. A device according to claim 1, wherein the size of each of the instrumental seals ranges from 5 mm to 12 mm.

11. A device according to claim 1, wherein the distal ring-shaped portion includes an O-ring.

12. A device according to claim 11, wherein the retraction portion includes a retracting sleeve.

13. A device according to claim 12, wherein the retracting sleeve extends in two layers between the distal ring-shaped portion and the proximal ring-shaped portion.

14. An instrument access device comprising:
   a wound retractor including:
      a proximal ring-shaped portion for location externally of a wound opening;
      a distal ring-shaped portion for location within a wound interior;
      a retraction portion extending proximally from the distal portion to the proximal portion to retract laterally the sides of the wound opening; and
   a seal assembly including:
      a first instrument seal spaced proximally the proximal ring-shaped portion of the wound retractor and laterally movable with respect to the proximal ring-shaped portion;
      a second instrument seal spaced proximally the proximal ring-shaped portion of the wound retractor and laterally movable with respect to the proximal ring-shaped portion;
      a third instrument seal spaced proximally the proximal ring-shaped portion of the wound retractor and laterally movable with respect to the proximal ring-shaped portion
      a fourth instrument seal spaced proximally the proximal ring-shaped portion of the wound retractor and laterally movable with respect to the proximal ring-shaped portion; and
      the first instrument seal being larger than the second, third, and fourth instrument seals; the second and third instrument seals having substantially the same size; the first, second, and third instrument seals being orientated in a generally triangular at-rest configuration; and the fourth instrument seal being located between the second and third instrument seals.

15. A device according to claim 14, wherein the seal assembly further includes separate, proximally extending connector tubes coupled to respective instrument seals.

16. A device according to claim 15, wherein each of the connector tubes is laterally flexible.

17. A device according to claim 15, wherein each of the connector tubes is oblique to one another and oblique to a longitudinal axis of the wound retractor.

18. A device according to claim 15, wherein each of the connector tube is longitudinally rigid.

19. A device according to claim 14, further including a connector base portion configured to releasably mount the seal assembly to the proximal ring-shaped portion.

20. A device according to claim 19, wherein the connector base portion includes a proximally extending dome portion.

21. A device according to claim 19, wherein the connector base portion includes a radially outer protruding member configured to engage with a radially inner part of the proximal ring-shaped portion.

22. A device according to claim 14, wherein the distal ring-shaped portion includes an O-ring.

23. A device according to claim 14, wherein the retraction portion includes a retracting sleeve.

24. A device according to claim 23, wherein the retracting sleeve extends in two layers between the distal ring-shaped portion and the proximal ring-shaped portion.

25. An instrument access device comprising:
   a wound retractor including:
      a proximal ring-shaped portion for location externally of a wound opening;
      a distal ring-shaped portion for location within a wound interior;
      a retraction portion extending proximally from the distal portion to the proximal portion to retract laterally the sides of the wound opening; and
   a seal assembly including:
      a first instrument seal spaced proximally the proximal ring-shaped portion of the wound retractor and laterally movable with respect to the proximal ring-shaped portion;

a second instrument seal spaced proximally the proximal ring-shaped portion of the wound retractor and laterally movable with respect to the proximal ring-shaped portion;

a third instrument seal spaced proximally the proximal ring-shaped portion of the wound retractor and laterally movable with respect to the proximal ring-shaped portion a fourth instrument seal spaced proximally the proximal ring-shaped portion of the wound retractor and laterally movable with respect to the proximal ring-shaped portion; and the first instrument seal being larger than the second, third, and fourth instrument seals; the second and third instrument seals having substantially the same size; the first, second, and third instrument seals being orientated in a generally triangular at-rest configuration; the fourth instrument seal being located between the second and third instrument seals; and the size of each of the instrumental seals ranges from 5 mm to 12 mm.

\* \* \* \* \*

UNITED STATES PATENT AND TRADEMARK OFFICE
CERTIFICATE OF CORRECTION

PATENT NO.       : 8,187,178 B2
APPLICATION NO.  : 12/133827
DATED            : May 29, 2012
INVENTOR(S)      : Frank Bonadio et al.

Page 1 of 1

It is certified that error appears in the above-identified patent and that said Letters Patent is hereby corrected as shown below:

In claim 14, col. 12, line 16, insert --;-- after "portion".

In claim 18, col. 12, line 37, "connector tube" should read --connector tubes--.

In claim 25, col. 13, line 8, insert --;-- after "portion".

Signed and Sealed this
Fourteenth Day of August, 2012

David J. Kappos
*Director of the United States Patent and Trademark Office*